(12) United States Patent
Miller et al.

(10) Patent No.: US 12,169,832 B2
(45) Date of Patent: *Dec. 17, 2024

(54) METHOD AND APPARATUSES FOR INTERACTIVE ORDERING OF DENTAL APPLIANCES

(71) Applicant: Align Technology, Inc., San Jose, CA (US)

(72) Inventors: Matthew Todd Miller, The Woodlands, TX (US); Douglas Fedich, Cary, NC (US); Leela Parvathaneni, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/141,110

(22) Filed: Jan. 4, 2021

(65) Prior Publication Data

US 2021/0342829 A1    Nov. 4, 2021

Related U.S. Application Data

(63) Continuation of application No. 16/038,088, filed on Jul. 17, 2018, now Pat. No. 10,885,521.

(60) Provisional application No. 62/533,625, filed on Jul. 17, 2017.

(51) Int. Cl.
| | | |
|---|---|---|
| *G06Q 20/40* | (2012.01) | |
| *A61C 7/00* | (2006.01) | |
| *A61C 7/08* | (2006.01) | |
| *G06Q 20/10* | (2012.01) | |
| *G06Q 40/08* | (2012.01) | |
| *G06Q 50/22* | (2018.01) | |
| *G16H 40/40* | (2018.01) | |
| *G16H 50/30* | (2018.01) | |
| *G16H 80/00* | (2018.01) | |

(52) U.S. Cl.
CPC ............ *G06Q 20/40* (2013.01); *A61C 7/002* (2013.01); *A61C 7/08* (2013.01); *G06Q 20/102* (2013.01); *G06Q 40/08* (2013.01); *G06Q 50/22* (2013.01); *G16H 40/40* (2018.01); *G16H 50/30* (2018.01); *G16H 80/00* (2018.01)

(58) Field of Classification Search
CPC ...... G06Q 20/40; G06Q 20/102; G06Q 40/08; G06Q 50/22; A61C 7/002; A61C 7/08; G16H 40/40; G16H 50/30; G16H 80/00
See application file for complete search history.

(56) References Cited

U.S. PATENT DOCUMENTS

| | | |
|---|---|---|
| 7,001,270 B2 | 2/2006 | Taub |
| 7,383,198 B1 | 6/2008 | Sepe |
| 7,580,846 B2 | 8/2009 | Chishti et al. |
| 7,870,280 B2 | 1/2011 | Kuo |
| 7,904,307 B2 | 3/2011 | Abolfathi et al. |
| 7,987,099 B2 | 7/2011 | Kuo et al. |
| 8,024,198 B2 | 9/2011 | Kuo |
| 8,738,394 B2 | 5/2014 | Kuo |
| 10,467,815 B2 | 11/2019 | Marom et al. |

(Continued)

*Primary Examiner* — Maroun P Kanaan
(74) *Attorney, Agent, or Firm* — Shay Glenn LLP

(57) ABSTRACT

Methods and apparatuses for interactive ordering of dental appliances. These methods generally include coordination of a dental appliance laboratory coordinating in the pre-approval process for financing the dental appliances, a financing server, and a dental practitioner (e.g., dentist, orthodontist, etc.).

29 Claims, 27 Drawing Sheets

(56) References Cited

U.S. PATENT DOCUMENTS

| | | |
|---|---|---|
| 10,504,386 B2 | 12/2019 | Levin et al. |
| 10,595,966 B2 | 3/2020 | Carrier, Jr. et al. |
| 10,695,150 B2 | 6/2020 | Kopelman et al. |
| 10,888,399 B2 | 1/2021 | Kopelman et al. |
| 10,980,612 B2 | 4/2021 | Jang |
| 10,980,613 B2 | 4/2021 | Shanjani et al. |
| 2001/0047307 A1* | 11/2001 | Bennett .................. G06Q 40/03 705/26.1 |
| 2002/0188478 A1 | 12/2002 | Breeland et al. |
| 2005/0159986 A1 | 7/2005 | Breeland et al. |
| 2008/0288289 A1 | 11/2008 | Sah |
| 2010/0068672 A1* | 3/2010 | Arjomand ................ A61C 7/00 433/24 |
| 2012/0221349 A1* | 8/2012 | Mora ..................... G16H 50/70 705/2 |
| 2017/0046709 A1* | 2/2017 | Lee ....................... G06Q 20/367 |
| 2020/0160947 A1 | 5/2020 | Rasovsky et al. |

* cited by examiner

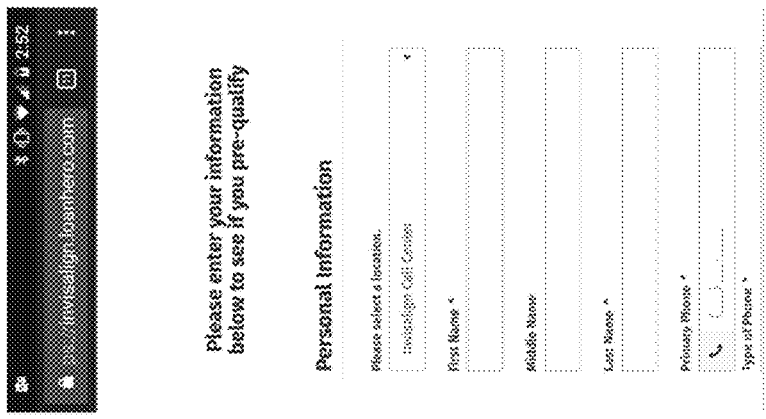
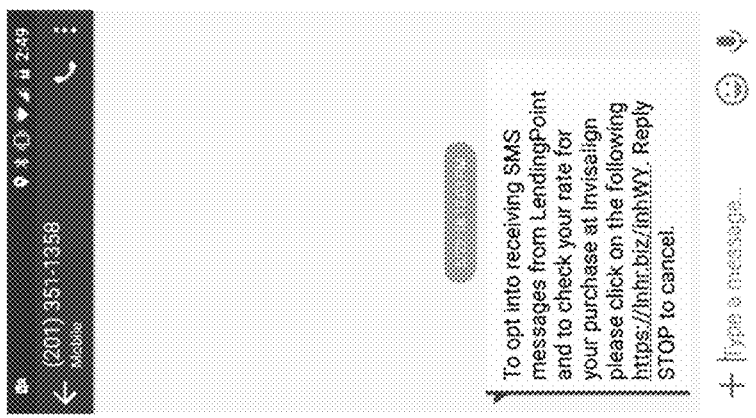
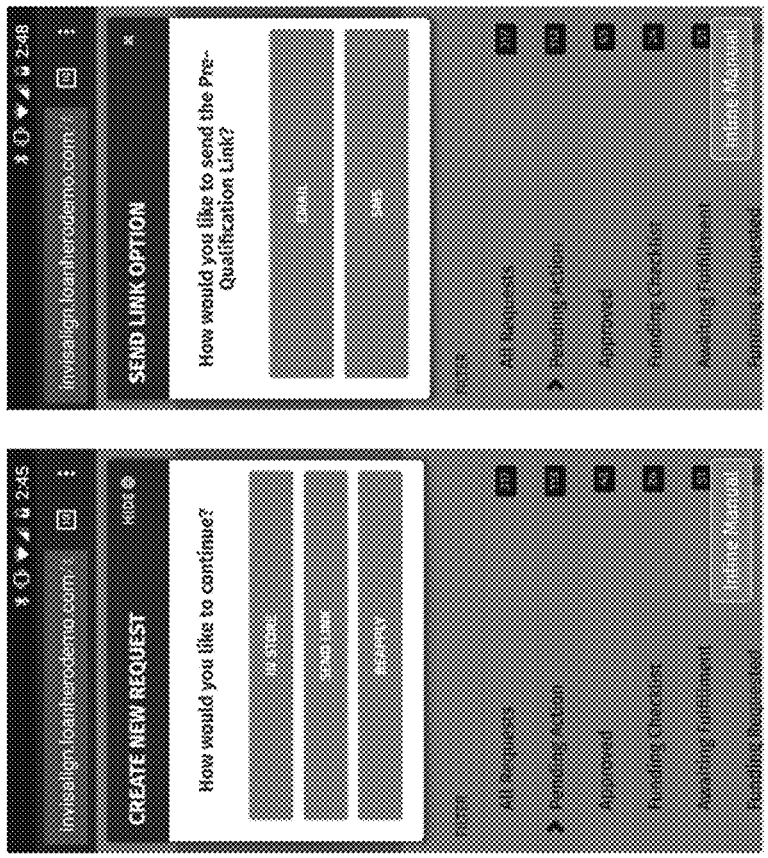
FIG. 3A1    FIG. 3A2    FIG. 3B    FIG. 3C
Practice can have consumer apply in the practice or send a link to the consumer to apply.
Consumer receives link and can fill out a short application on any device (cell phone, tablet, or computer)

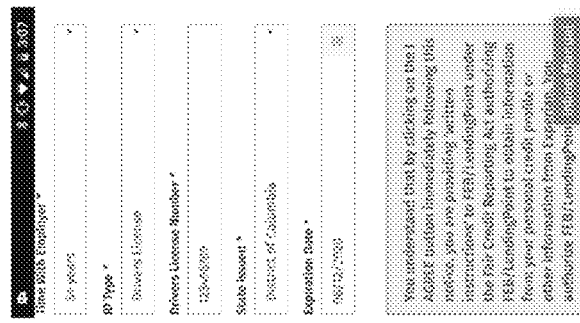
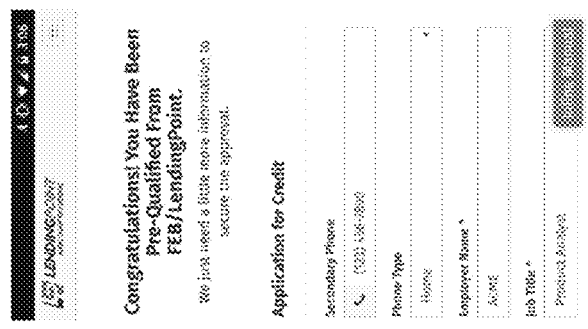
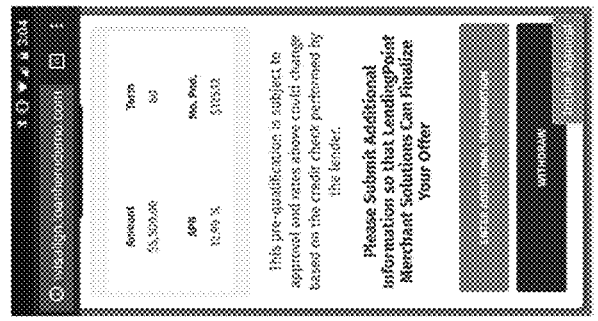
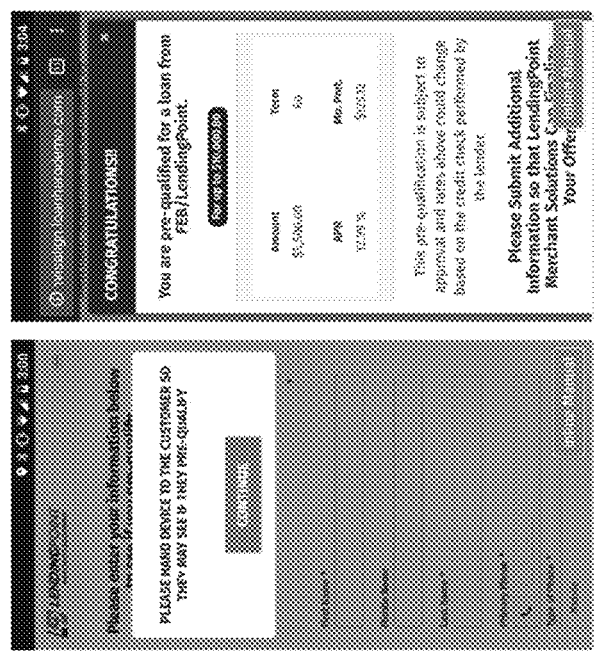
FIG. 4A   FIG. 4B   FIG. 4C   FIG. 4D   FIG. 4E

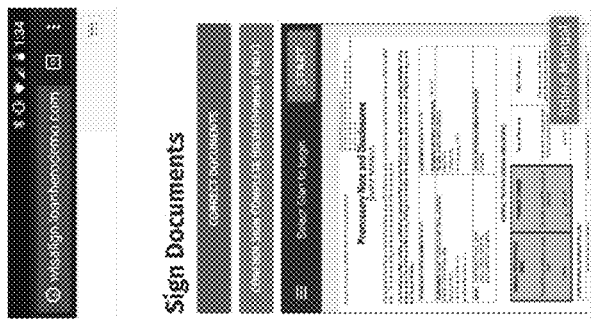
FIG. 4F
FIG. 4G
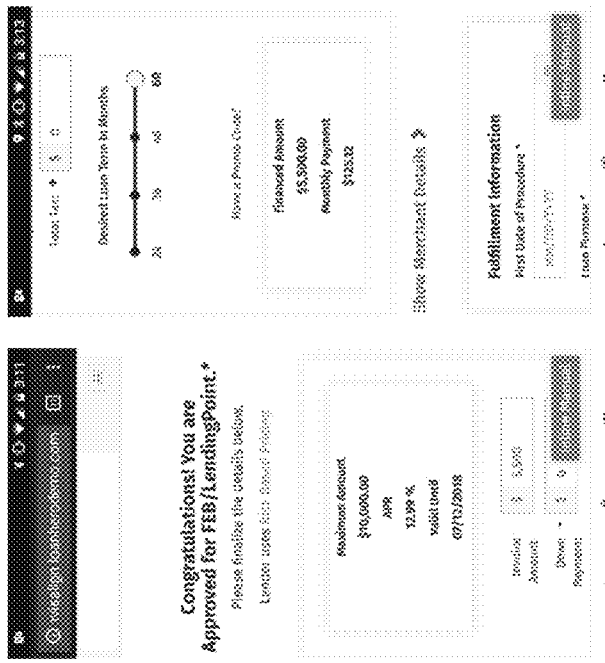
FIG. 4H
FIG. 4I

METHOD AND APPARATUSES FOR INTERACTIVE ORDERING OF DENTAL APPLIANCES

CROSS REFERENCE TO RELATED APPLICATIONS

This patent application is a continuation of U.S. patent application Ser. No. 16/038,088, filed on Jul. 17, 2018, which claims priority to U.S. Provisional Patent Application No. 62/533,625, filed on Jul. 17, 2017, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontic treatments may include the use of a series of dental aligners for treating, and in particular for aligning, a patient's teeth. Typical treatments with dental aligners require a series of dental aligners that are sequentially worn. Such aligners have numerous advantages compared to more traditional braces formed by wires and brackets, including ease of use, effectiveness, and aesthetics.

One common barrier for all orthodontic treatment is the cost, and the current manner in which such treatments may be financed. Often, dental practitioners, such as orthodontists, dentists, etc. must provide financing plans at their own expense and risk, particularly with respect to aligners. Larger financing entities and services that could provide patient's loans for such treatments may place additional burdens on the dental practitioner, including financial disincentives.

Thus, the current methods for financing orthodontic treatments such as aligners may place an undue burden on dental practitioners, particularly those having smaller practices and those serving less affluent communities. This may result in a disproportionate bias for providing less expensive, and often less effective, treatments. Further, requiring the dental practitioner to shoulder the burden of either self-financing or acting as the primary interface with third party financing organizations is inefficient, particularly in respect to dental aligners, in which the dental aligner laboratory, which actually designs and manufactures the aligners at the instruction of the dental practitioner.

Described herein are methods and apparatuses that may address these issues.

SUMMARY OF THE DISCLOSURE

The present invention relates broadly to methods of manufacturing a series of dental aligners for a patient. These methods also includes methods of preparing to manufacture a series of dental aligners, and methods of financing dental aligners.

In general, these methods, and apparatuses (e.g., systems and devices, including software, hardware and firmware that may perform any of the methods described herein) may operate between a dental aligner laboratory ("lab"), a patient (e.g., a "putative patient" preparing for, or considering, treatment using a series of aligners), one or more dental practitioners (e.g., dentists, orthodontists, dental technicians, etc.), and a third-party financing service (including a service maintained by financial server that may automatically approve and/or service a patient loan). A database (e.g., a database of putative patient loan information) may be maintained by the third party financing service. The dental aligner laboratory may have a first level of access (e.g., "master" access) to this database, while the one or more dental practitioners may be have a second level of access (e.g., "client" access, e.g., as clients of the dental aligner laboratory). This configuration may allow the dental aligner laboratory to streamline patient care including the manufacture of the series of aligners.

In the methods and apparatuses described herein, the dental aligner laboratory (manufacturer) may monitor the database of the third party financing service, allowing immediate feedback on patient status and orders. This permits the more efficient manufacture and distribution of aligners than was previously possible. By modifying the financial relationship between the consumer (putative patient), medical device manufacturer (dental aligner laboratory), and the healthcare provider (dental practitioner), the dental practitioner does not receive invoices from the manufacturer. Instead, the provider may receive revenue at the time that treatment is provided to the patient, e.g., when providing aligners that have already been manufactured to fit the patient as specified by the dental practitioner. This may reduce or eliminate substantial financial barriers and may also enhance the process of manufacturing and delivering a series of aligner to individual patients.

For example, a putative patient may finance treatment with a series of aligners using a third party, but controlled and facilitated through the dental aligner laboratory instead of the provider. Thus, the dental aligner laboratory may coordinate the financing in conjunction with the preparation for treatment. This both frees up the dental practitioner, but may also be particularly advantageous when preparing for treatment with a series of dental aligners, as such treatment is often front-loaded, in that is there is an initial design and manufacturing period before treatment may begin. The methods described herein may allow the dental aligner laboratory, to prepare for such treatments earlier in the process than in currently possible.

At the point of treatment, the putative patient's treatment costs may be funded at least in part through a consumer credit loan provided by a third party. The methods and apparatuses described herein also allow the provider to be paid for services rendered at the time the dental aligners are provided to the patient.

As will be described more fully below, upon the funding of a consumer credit loan by the third party financing service, the funds may be divided between the dental aligner laboratory (manufacturer) and the provider. For example; the laboratory fees, less any discounts provided to the dental practitioner/patient may be paid in parallel with the payments to the dental practitioner. These fee payments may be remitted (e.g., electronically by ACH) to the dental aligner laboratory and to the dental practitioner delivering the services to the patient. These methods and apparatuses for performing them may therefore remove or greatly reduce financial barriers that otherwise limit the dental practitioner from using dental aligners to benefit patients due to upfront costs and the burden of self-financing or coordinating financing. From the perspective of the dental practitioner, the methods described herein may remove these costs; rather than receiving invoices from the dental aligner laboratory, they may instead receive payments, as the dental aligner laboratory coordinates these payments. At the same time, these methods may allow the dental aligner laboratory (manufacturer) to streamline production and processing of patient orders, which may in turn reduce costs.

Thus, described herein are methods of manufacturing a series of aligners. These methods may include: receiving, from a putative patient, a patient information and a request for financing of a series of dental aligners; pre-approving the putative patient for a maximum financed amount and entering the patient information, a preapproval status, and the maximum financed amount into a database; transmitting an alert to a dental aligner laboratory when the putative patient is pre-approved so that the dental aligner laboratory may prepare to manufacture aligners for the putative patient; receiving a preapproval status inquiry from a dental practitioner on behalf of the putative patient, and transmitting the preapproval status and maximum financed amount from the database to the dental practitioner; receiving a treatment cost from the dental practitioner for treating the putative patient and including it in the database; transmitting, to the dental aligner laboratory, an alert when the treatment cost is received along with information identifying the dental practitioner; receiving, from the dental aligner laboratory, a laboratory cost; receiving, from the putative patient, acceptance of an actual financed amount and updating the database to indicate funding of the actual financed amount; transmitting an alert to a dental aligner laboratory that the database has been updated to indicate funding of the actual financed amount so that the dental aligner laboratory may manufacture the series of aligners; and paying, upon receiving notification from the dental aligner laboratory that the series of dental aligners has been sent, a first portion of the actual financed amount to the dental aligner laboratory and a second portion (in some implementations, a remainder) of the actual financed amount to the dental practitioner.

This method may be performed, for example, by a third party financing service and may be partially or completely automated. Thus, these methods may be performed by a financing server including one or more processor configured to execute these steps, and/or control and coordinate the database (e.g., the database of putative loan information). Thus, in any of these methods, receiving the patient information and request for financing, the treatment cost, the laboratory cost, and the acceptance of the actual financed amount may include receiving in a remote processor.

The putative patient may be presented with loan information and/or dental information (including payment plans) on a handheld device. For example, any of these methods may include presenting to the putative patient a user interface on the putative patient's handheld mobile device (e.g., phone, smartphone, tablet, smartwatch, etc.) that is configured to receive the patient information and a request for financing of a series of dental aligners, wherein the user interface communicates with a remote processor.

Receiving the patient information may include receiving one or more of: a patient identifying code identifying the putative patient, the putative patient's name, the putative patient's address, the putative patient's age. In general, patient information may include information sufficient to complete a check of the putative patient's credit. Patient dental information may include information (e.g., images, scans, dental records, etc.) specific to the patient's oral cavity, including teeth, etc. Patient dental information may be a subset of patient information.

Any of these methods may also include adjusting the maximum financed amount at the request of the dental aligner laboratory, wherein the dental aligner laboratory calculates a treatment risk specific to the putative patient based on one or more of a scan of the putative patient's teeth and the patient information. The treatment risk may alternatively or additionally be based on an estimated compliance score. For example, based on a patient's age and/or gender, a score regarding compliance may be determined. Patient's having a higher compliance score (e.g., treatment or dental treatment compliance) may therefore be more likely to successfully complete the treatment.

Any of these methods may also be configured to provide master access to the database to the dental aligner laboratory; one or more dental practitioners may be given client access to the database. Typically, master access may control the client access and may provide greater access and the ability to search, edit and monitor the database. Client access may be more limited, e.g., allowing patient-specific queries and access.

Transmitting the alert (e.g., notification, etc.) to the dental aligner laboratory when the putative patient is pre-approved may include transmitting the alert to the dental aligner laboratory so that dental aligner laboratory may prepare to manufacture aligners for the putative patient by preparing to receive dental information specific to the putative patient from the putative patient and/or the putative patient's dental practitioner. In general, preparing to manufacture aligners for the putative patient may include monitoring the patient record in the database, contact the putative patient (e.g., requesting additional information from the putative patient, providing additional information on the treatment to the putative patient, etc.). For example, preparing to manufacture aligners for the putative patient may include requesting dental information about the putative patient from the patient directly and/or from the dental practitioner or other source. In some variations, the requested dental information may include one or more of: an image of the putative patient's teeth, a digital scan of the putative patient's teeth, and a copy of the putative patient's dental record. Preparing to manufacture aligners for the putative patient may include referring the putative patient to a dental practitioner.

In general, the methods described herein may include receiving the laboratory cost. This may include receiving laboratory costs (e.g., from the dental aligner laboratory) based on the identity of the dental practitioner and/or based on dental information about the putative patient. For example, the dental aligner laboratory may determine the laboratory costs based on the treatment plan specific to the putative patient, and/or based on the identity of the dental practitioner. The dental aligner laboratory may provide one or more discounts on the series of aligners based on the identity of the patient and/or promotions for the putative patient and/or dental practitioner.

As mentioned, a user interface for the consumer (putative patient) may include a mobile application software that communicates with the third party financing and/or the dental aligner laboratory through the putative patient's electronics device. For example, any of these methods may also include providing, in a user interface on the putative patient's mobile device, a choice of financing options before receiving acceptance of the actual financed amount.

A method of manufacturing a series of aligners may include: receiving, from a putative patient, a request for financing of a series of dental aligners in a remote processor having a database to which a dental aligner laboratory has master access and further to which a dental practitioner has client access, wherein the request for financing includes patient information specific to the putative patient; pre-approving the putative patient for a maximum financed amount and entering the patient information, a preapproval status, and the maximum financed amount into the database; transmitting an alert to the dental aligner laboratory when the putative patient is pre-approved so that dental aligner laboratory may prepare to manufacture aligners for the putative patient; receiving a preapproval status inquiry from the dental practitioner on behalf of the putative patient, and transmitting the preapproval status and maximum financed amount from the database to the dental practitioner; receiving a treatment cost for treating the putative patient and including it in the database; receiving a laboratory cost for treating the putative patient; receiving, from the putative patient, acceptance of an actual financed amount and updating the database to indicate funding of the actual financed amount; initiating manufacture of the series of dental aligners specific to the putative patient by transmitting an alert to a dental aligner laboratory that the actual financed amount has been funded; paying, following receipt of notification that the series of dental aligners has been completed and sent, a first portion of the actual financed amount to the dental aligner laboratory and a second portion (e.g., a remainder) of the actual financed amount to the dental practitioner.

A method of manufacturing a series of aligners may include: receiving, from a putative patient, a request for financing of a series of dental aligners in a remote processor having a database to which a dental aligner laboratory has master access and further to which a dental practitioner has client access, wherein the request for financing includes patient information specific to the putative patient; pre-approving the putative patient for a maximum financed amount and entering the patient information, a preapproval status, and the maximum financed amount into the database; receiving a preapproval status inquiry from the dental practitioner on behalf of the putative patient, and transmitting the preapproval status and maximum financed amount from the database to the dental practitioner; receiving a treatment cost for treating the putative patient and including it in the database; receiving a laboratory cost for treating the putative patient; receiving, from the putative patient, acceptance of an actual financed amount and updating the database to indicate funding of the actual financed amount; initiating manufacture of the series of dental aligners specific to the putative patient by transmitting an alert to a dental aligner laboratory that the actual financed amount has been funded; paying, following receipt of notification that the series of dental aligners has been completed and sent, a first portion of the actual financed amount to the dental aligner laboratory and a second portion (e.g., a remainder) of the actual financed amount to the dental practitioner.

Also described herein are methods of manufacturing a series of dental aligners (or methods of preparing to manufacture a series of dental aligners) that are performed primarily or exclusively by the dental aligner laboratory in conjunction with the third party financing service (e.g., automated financial server), putative patient and one or more (e.g., a plurality of) dental practitioners.

For example, a method of manufacturing a series of dental aligners may include: providing master access to a database of putative patient loan information to a dental aligner laboratory; receiving, by the dental aligner laboratory, a notification from a remote financing server that a putative patient has requested or received pre-approval of a maximum financed amount for a dental aligner treatment and preparing to manufacture the series of aligners for the putative patient upon receiving the notification; receiving, by the dental aligner laboratory, an alert when the remote financing server receives a treatment cost from a dental practitioner for the putative patient; calculating a laboratory cost for manufacturing the series of aligners for the putative patient and transmitting the laboratory cost to the remote financing server; receiving an alert that the remote financial server has funded an actual financed amount for the putative patient and thereafter initiating manufacture of the series of dental aligners specific to the putative patient; and transmitting instructions to the remote financial server to pay the treatment cost to the dental practitioner and to pay the laboratory cost to the dental aligner laboratory after the series of dental aligners has been completed and sent.

As mentioned, preparing to manufacture the series of aligners for the putative patient may comprise preparing to receive dental information specific to the putative patient from the putative patient and/or the putative patient's dental practitioner, and/or requesting dental information about the putative patient (e.g., requesting one or more of: an image of the putative patient's teeth, a digital scan of the putative patient's teeth, and a copy of the putative patient's dental record, and/or requesting from the dental practitioner that is associated with the putative patient in the database of putative patient loan information); and or referring the putative patient to a dental practitioner.

Receiving, by the dental aligner laboratory, an alert may comprise receiving a request for laboratory cost. Calculating the laboratory cost for manufacturing the series of aligners for the putative patient may be based a discount associated with the dental practitioner and/or the putative patient's dental information.

Any of these methods may also include transmitting, to the remote financing server from the dental aligner laboratory, an adjusted maximum financed amount based a treatment risk for the putative patient. For example, any of these methods may include adjusting the maximum financed amount based on a treatment risk determined using patient dental information comprising one or more of: an image of the putative patient's teeth, a digital scan of the putative patient's teeth.

A method of manufacturing a series of dental aligners may include: providing master access to a database of putative patient loan information to a dental aligner laboratory; monitoring, by the dental aligner laboratory, a database (e.g., database of putative patient loan information) maintained by a remote financing server from which a putative patient has requested or received pre-approval of a maximum financed amount for a dental aligner treatment; receiving, by the dental aligner laboratory, an alert when the remote financing server receives a treatment cost from a dental practitioner for the putative patient; calculating a laboratory cost for manufacturing the series of aligners for the putative patient and transmitting the laboratory cost to the remote financing server; receiving an alert that the remote financial server has funded an actual financed amount for the putative patient and thereafter initiating manufacture of the series of dental aligners specific to the putative patient; and transmitting instructions to the remote financial server to pay the treatment cost to the dental practitioner and to pay the laboratory cost to the dental aligner laboratory after the series of dental aligners has been completed and sent.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A1-3E illustrate an exemplary patient user interface that may be used (e.g., as part of a mobile application or other software) during the pre-approval portion of the methods of fabricating a series of aligners as described herein.

FIGS. 4A-4I illustrate an exemplary patient user interface that may be used to select and approve a treatment loan as described herein.

FIG. 6 is an example of a user interface for monitoring an Approval Database (e.g., monitoring by Master (e.g., Lab) and/or Client (e.g., Dental Physician).

FIGS. 13A and 13B show example of user interfaces for a transfer process in a third party loan application.

DETAILED DESCRIPTION

The methods and apparatuses described herein generally allow a dental aligner laboratory (e.g., a dental aligner laboratory associated with a dental aligner manufacturer) 160 to monitor a database of the third party financing service 180, allowing immediate feedback on patient (putative patient 155) status and orders. FIG. 1 gives an overview of possible relationships between the dental aligner laboratory 160, putative patient 155, dental practitioner(s) 170, 170', and third party financing service 180.

The dental aligner manufacturer may coordinate the process manufacturing a series of aligners on behalf of a putative patient including the important pre-manufacturing steps of financing and pre-screening of putative patients before a therapy is started. Therapy typically starts when the aligners are provided to the putative patient, e.g., by the dental practitioner. Described herein are methods in which the dental aligner laboratory (rather than the dental practitioner and/or the third party financing service) coordinates the financing of the treatment. This may permit the more efficient manufacture and distribution of aligners than was previously possible. This may reduce or eliminate substantial financial barriers and may also enhance the process of manufacturing and delivering a series of aligner to individual patients.

Figure 17:
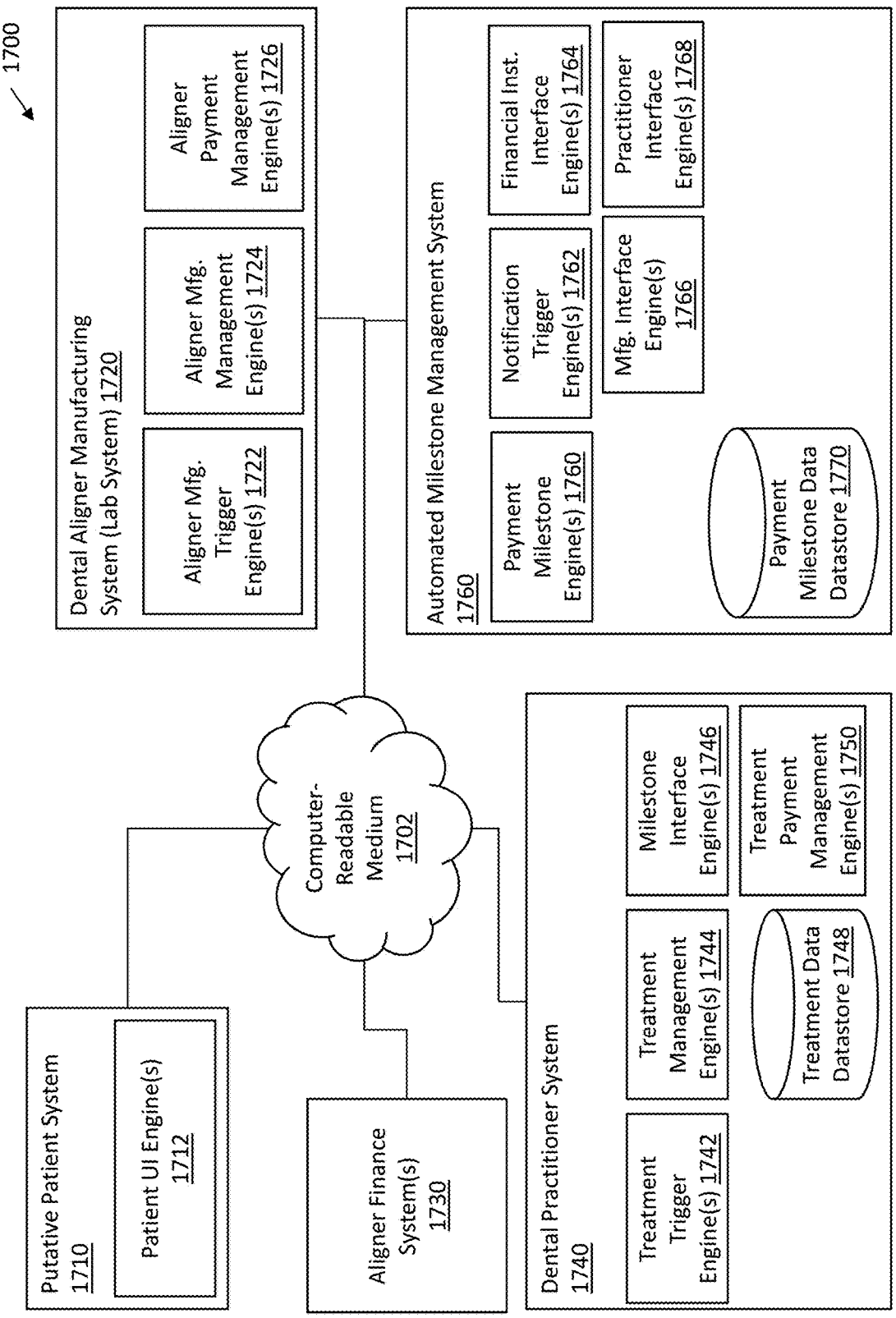
FIG. 17 shows an example of a coordinated aligner payment alert environment, in accordance with some implementations.

FIG. 17 shows an example of a coordinated aligner payment alert environment 1700, in accordance with some implementations. The coordinated aligner payment alert environment 1700 may include a computer-readable medium 1702, a putative patient system 1710, a dental aligner manufacturing system 1720 (alternatively referred to herein as a laboratory system), aligner finance system(s) 1730, a dental practitioner system 1740, and an automated milestone management system 1760. One or more of the elements of the coordinated aligner payment alert environment 1700 may be coupled to one another or to modules not explicitly shown in FIG. 17. As an example, the elements of the coordinated aligner payment alert environment 1700 may be coupled to one another through the computer-readable medium 1702.

As further discussed herein, the elements of the coordinated aligner payment alert environment 1700 may operate to provide distributed, coordinated, and/or real-time alert about the status of payment milestone, such as a financing and/or payment milestone for one or more orthodontic aligners. As noted herein, the elements of the coordinated aligner payment alert environment 1700 may further operate to route payment from the aligner finance system(s) 1730 and to split a payment for orthodontic treatment between the dental aligner manufacturing system 1720 and the dental practitioner system 1740. The components herein operate in an unconventional manner to achieve various improvements in computer functionality, such as the provision of distributed, coordinated, and/or real-time alert about the status of payment milestone without any human intervention. The automated agents implemented by the elements of the coordinated aligner payment alert environment 1700 may work together in a distributed manner to enhance the provisioning of data in a distributed fashion and therefore may facilitate solving significant technical problems related to managing massive payment data record flows related to orthodontic treatments and/or aligners.

The computer-readable medium 1702 and other computer readable media discussed in this paper are intended to represent a variety of potentially applicable technologies. For example, the computer-readable medium 1702 can be used to form a network or part of a network. Where two components are co-located on a device, the computer-readable medium 1702 can include a bus or other data conduit or plane. Where a first component is co-located on one device and a second component is located on a different device, the computer-readable medium 1702 can include a wireless or wired back-end network or LAN. The computer-readable medium 1702 can also encompass a relevant portion of a WAN or other network, if applicable. As noted herein, the computer-readable medium 1702 may be configured to couple one or more of the elements of the coordinated aligner payment alert environment 1700 to one another. In this example, the computer-readable medium 1702 couples the putative patient system 1710, the dental aligner manufacturing system 1720 (alternatively referred to herein as a laboratory system), the aligner finance system(s) 1730, the dental practitioner system 1740, and the automated milestone management system 1760 to one another.

The putative patient system 1710 may include a digital device configured to interface with a putative patient and/or a patient. The putative patient may be a person seeking orthodontic treatment of an orthodontic condition, e.g., through the use of orthodontic aligners. The putative patient system 1710 may include a patient user interface (UI) engine 1712. The patient UI engine 1712 may be configured to receive user input and/or display results of user input, treatment data, and/or financial data to a putative patient.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The dental aligner manufacturing system 1720 may include a digital device configured to facilitate design and/or manufacture of orthodontic aligners. The dental aligner manufacturing system 1720 may include aligner manufacture engine(s) 1722, aligner manufacture management engine(s) 1724, and aligner payment management engine(s) 1726. One or more elements of the dental aligner manufacturing system 1720 may be coupled to one another or to modules not explicitly shown. The dental aligner manufacturing system 1720 may be managed and/or associated with an entity that makes orthodontic aligners.

The aligner manufacture trigger engine(s) 1722 may implement one or more automated agents configured to manage aligner manufacture triggers. An "aligner manufacture trigger," as used herein, may include computer program instructions and/or code configured to trigger instructions to manage aligner manufacturing parameters. Aligner manufacture triggers may be based on or coordinated with achievement of a payment milestone. A "payment milestone," as used herein, may include an event related to fulfillment of a condition to pay for aligners. Examples of payment milestones include achievement of pre-approval (e.g., pre-qualification or qualification for a loan for aligners) by a customer, satisfaction of an obligation to pay a portion of a debt related to aligners (e.g., payment of a down payment related to a loan for aligners), etc. As noted herein, payment milestones may be provided in the form of notification triggers from the automated milestone management system 1760.

Coordination of aligner manufacturing may provide a substantial improvement in reducing the time to deliver the aligners as well as in generating, validating and confirming individual treatment plans, particularly as the number of patients to be treated increases. Fabrication or manufacture of aligners may include a variety of steps, including iteration between the dental practitioner (e.g., dentist, orthodontist, etc.) and the laboratory. Prior to fabrication of the aligner(s) by the laboratory and delivery of the sequence of aligner to an individual patient by the dental practitioner and/or laboratory, the dental practitioner must customize the treatment plan to each individual patient. This customization must take into account both the skill and desires of the dental practitioner and the constraints of the manufacturing process; thus, each treatment plan may represent a substantial amount of up-front customization to each individual patient and coordination between the dental practitioner and the laboratory. However, the dental practitioner and laboratory are usually economically independent agents; neither the dental practitioner nor the laboratory may desire to shoulder the burden of undertaking the aligner manufacture process (including treatment planning, validation, finalization and fabrication of a series of aligner), particularly at early stages, during which the risk of default is highest. The methods and systems, including the coordinated aligner payment alert environment 1700, described herein provide a solution to the highly technical problem of manufacturing dental aligners by distributing the financial and fabrication portions of the fabrication process more equitably between the dental practitioner and laboratory.

The aligner manufacture management engine 1724 may implement one or more automated agents configured to implement instructions to manufacture aligners. The aligner manufacture management engine 1724 may be configured to instruct a 3D printer to form an aligner mold and/or to directly fabricate aligners. The aligner manufacture management engine 1724 may be configured to instruct a thermoforming system to thermoform aligners over an aligner mold. In some implementations, the aligner manufacture management engine 1724 may be configured to receive instructions from the aligner manufacture trigger engine(s) 1722. As an example, the aligner manufacture management engine 1724 may be configured to receive aligner manufacture triggers, such as those based on achievement of a payment milestone, from the aligner manufacture trigger engine(s) 1722. The aligner manufacture management engine 1724 may further be configured to base instructions to fabricate aligners and/or aligner molds based on aligner manufacture triggers.

The aligner payment management engine(s) 1726 may implement one or more automated agents configured to monitor a payment status of aligners. The aligner payment management engine(s) 1726 may be configured to identify whether or not an aligner manufacturer has been paid (and/or otherwise contractually satisfied) for aligners. The aligner payment management engine(s) 1726 may be configured to receive at least a portion of payment for aligners from, e.g., the aligner finance system(s) 1730 and/or the automated milestone management system 1760. In some implementations, the notification triggers from the automated milestone management system 1760 may include instructions to transfer payment for aligners from the aligner finance system(s) 1730.

The aligner finance system(s) 1730 may include a digital device configured to manage financing of aligners. The aligner finance system(s) 1730 may be maintained by financial entities, such as banks or loan providers. In some implementations, the aligner finance system(s) 1730 are maintained by "third-parties," e.g., entities other than a customer, a dental practitioner, and an aligner manufacturer. As a result, the aligner finance system(s) 1730 may incorporate one or more interfaces (not shown) that facilitate gathering of a person's financial data. The aligner finance system(s) 1730 may further comprise one or more engines and/or datastores that manage a putative patient's financial arrangements for obtaining aligners, e.g., loans for aligners.

The dental practitioner system(s) 1740 may include a digital device configured to instruct a dental practitioner to implement orthodontic aligner treatment. The dental practitioner system(s) 1740 may include treatment trigger engine(s) 1742, treatment management engine(s) 1744, milestone interface engine(s) 1746, a treatment data datastore 1748, and treatment payment management engine(s) 1750. One or more of the elements of the dental practitioner system 1740 may be coupled to one another or to components not explicitly shown. The dental practitioner system(s) 1740 may be managed and/or associated with an entity that implements orthodontic treatment (e.g., an orthodontist or orthodontist group).

The treatment trigger engine(s) 1742 may implement one or more automated agents configured to identify and/or manage treatment triggers. A "treatment trigger," as used herein, may include computer program instructions and/or code configured to trigger instructions to provide orthodontic treatment. A treatment trigger may, but need not, be related to achievement of a payment milestone. A treatment trigger may be related to attributes of orthodontic treatment (such as whether a putative patient needs/qualifies for orthodontic treatment), attributes of a putative patient, and/or other factors.

The treatment management engine(s) 1744 may implement one or more automated agents configured to implement an orthodontic treatment plan. The treatment management engine(s) 1744 may base treatment on treatment data from the treatment data datastore 1748. In some implementations, orthodontic treatment plans are based on satisfaction of treatment triggers. As an example, in some implementations, the treatment management engine(s) 1744 bases treatment plans on satisfaction of payment milestones, as further discussed herein.

The milestone interface engine(s) 1746 may implement one or more automated agents configured to interface with the automated milestone management system 1760. The milestone interface engine(s) 1746 may implement Application Programming Interfaces (APIs) that receive notification triggers from the automated milestone management system 1760. As noted further herein, the notification triggers may signify achievement of payment milestones, e.g., achievement of pre-approval (e.g., pre-qualification or qualification for a loan for aligners) by a customer, satisfaction of an obligation to pay a portion of a debt related to aligners (e.g., payment of a down payment related to a loan for aligners), etc.

The treatment payment management engine(s) 1750 may implement one or more automated agents configured to monitor a payment status of an orthodontic treatment plan. The treatment payment management engine(s) 1750 may be configured to identify whether or not an orthodontic treatment provider has been paid (and/or otherwise contractually satisfied) for an orthodontic treatment plan (e.g., one implemented using aligners). The treatment payment management engine(s) 1750 may be configured to receive at least a portion of payment for aligners from, e.g., the aligner finance system(s) 1730 and/or the automated milestone management system 1760. In some implementations, the notification triggers from the automated milestone management system 1760 may include instructions to transfer payment for aligners from the aligner finance system(s) 1730.

The automated milestone management system 1760 may include a digital device configured to monitor achievement of payment milestones and provide notification triggers to the dental aligner manufacturing system 1720 and/or the dental practitioner system 1740. The automated milestone management system 1760 may include payment milestone engine(s) 1760, notification trigger engine(s) 1762, financial institution interface engine(s) 1764, manufacturer interface engine(s) 1766, practitioner interface engine(s) 1768, and a payment milestone data datastore 1770. One or more of the elements of the automated milestone management system 1760 may be coupled to one another or to components not explicitly shown.

The payment milestone engine(s) 1760 may implement one or more automated agents configured to determine whether or not a putative patient achieved a payment milestone. In some implementations, the payment milestone engine(s) 1760 evaluates financial data gathered from the aligner finance system(s) 1730 to see if a putative patient achieved one or more specified payment milestones. The payment milestone engine(s) 1760 may evaluate the satisfaction of various payment milestone conditions using payment data stored in the payment milestone data datastore 1770. In some implementations, the payment milestone engine(s) 1760 implement automated rules to split payments between the dental aligner manufacturing system 1720 and the dental practitioner system 1740. The specific amounts of a split may be based on attributes (e.g., costs or estimated market value(s)) of a treatment plan, of aligner manufacturer, etc.

The notification trigger engine(s) 1762 may implement one or more automated agents configured to provide notification triggers. A notification trigger," as used herein, may include computer program instructions and/or code configured to trigger instructions to indicate achievement of a payment milestone. In some implementations, the notification triggers are implemented as real-time electronic alerts to various systems, such as the dental aligner manufacturing system 1720 and/or the dental practitioner system 1740. The notification trigger engine(s) 1762 may also provide notification triggers to, e.g., the putative patient system 1710. The real-time electronic alerts may comprise emails, in-application notifications, text (SMS) or other notifications, operating system (OS) alerts, etc. The notification triggers may provide a distributed and/or coordinated framework to communicate the status of payment milestones to a dental aligner manufacturer and a dental practitioner. In various implementations, the notification triggers operate to automatically and without human intervention split payment for aligners between a dental aligner manufacturer and a dental practitioner. As an example, the notification triggers may operate to automatically route electronic payments from the aligner finance system(s) 1730 to the dental aligner manufacturing system 1720 and the dental practitioner system(s) 1740. The amounts of a specific payment split may depend on various rules maintained by the payment milestone engine(s) 1760.

The financial institution interface engine(s) 1764 may implement one or more automated agents configured to interface with the aligner finance system(s) 1730. The manufacturer interface engine(s) 1766 may implement one or more automated agents configured to interface with the dental aligner manufacturing system 1720. The practitioner interface engine(s) 1768 may implement one or more automated agents configured to interface with the dental practitioner system 1740.

Figure 1A:
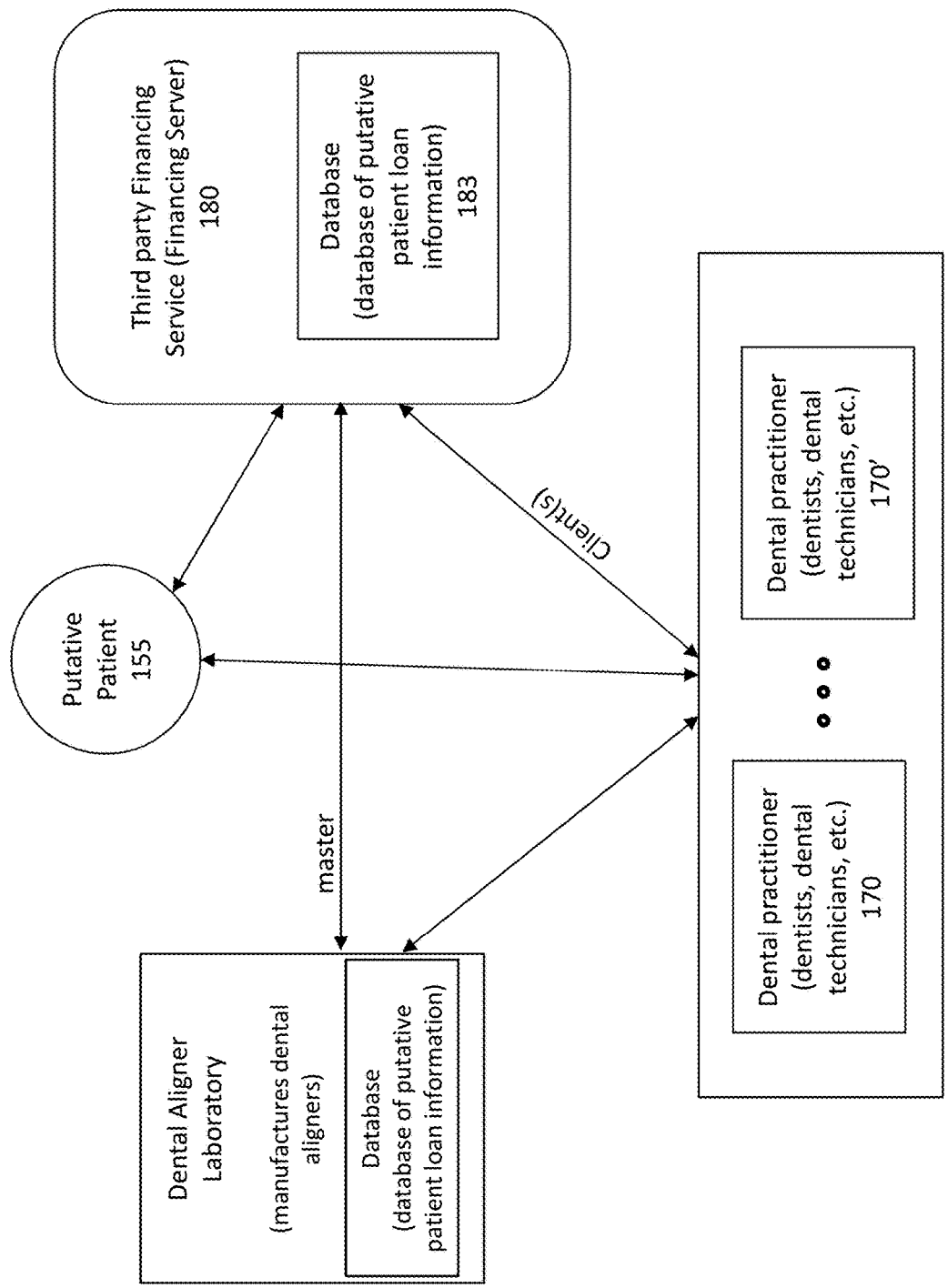
FIG. 1A illustrates the possible interactions between a dental aligner laboratory, a putative patient, a third party financing service, and one or more dental practitioners.
Figure 1B:
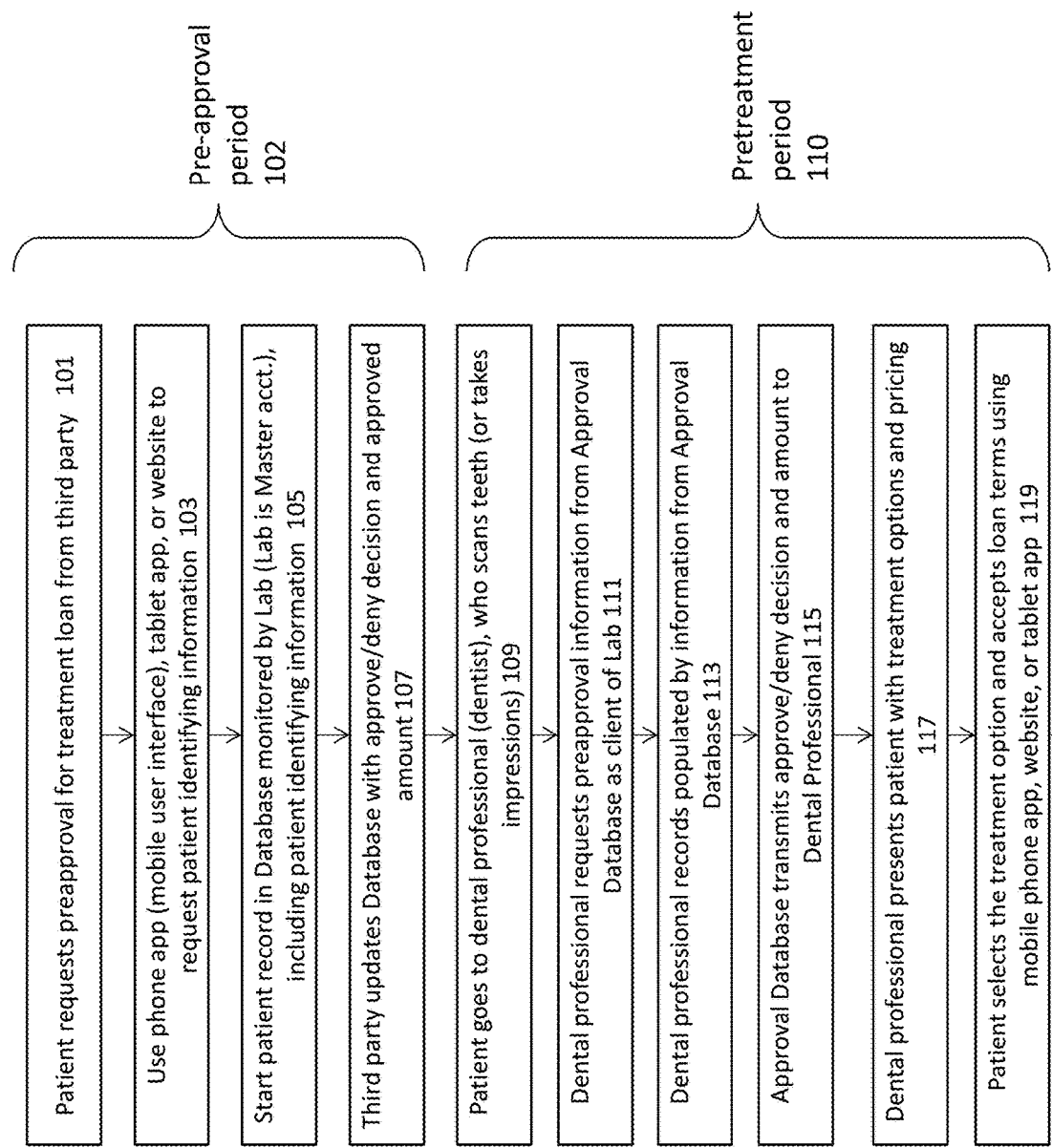
FIG. 1B is a first part of a flow diagram illustrating a method of fabricating a series of aligners.
Figure 1C:
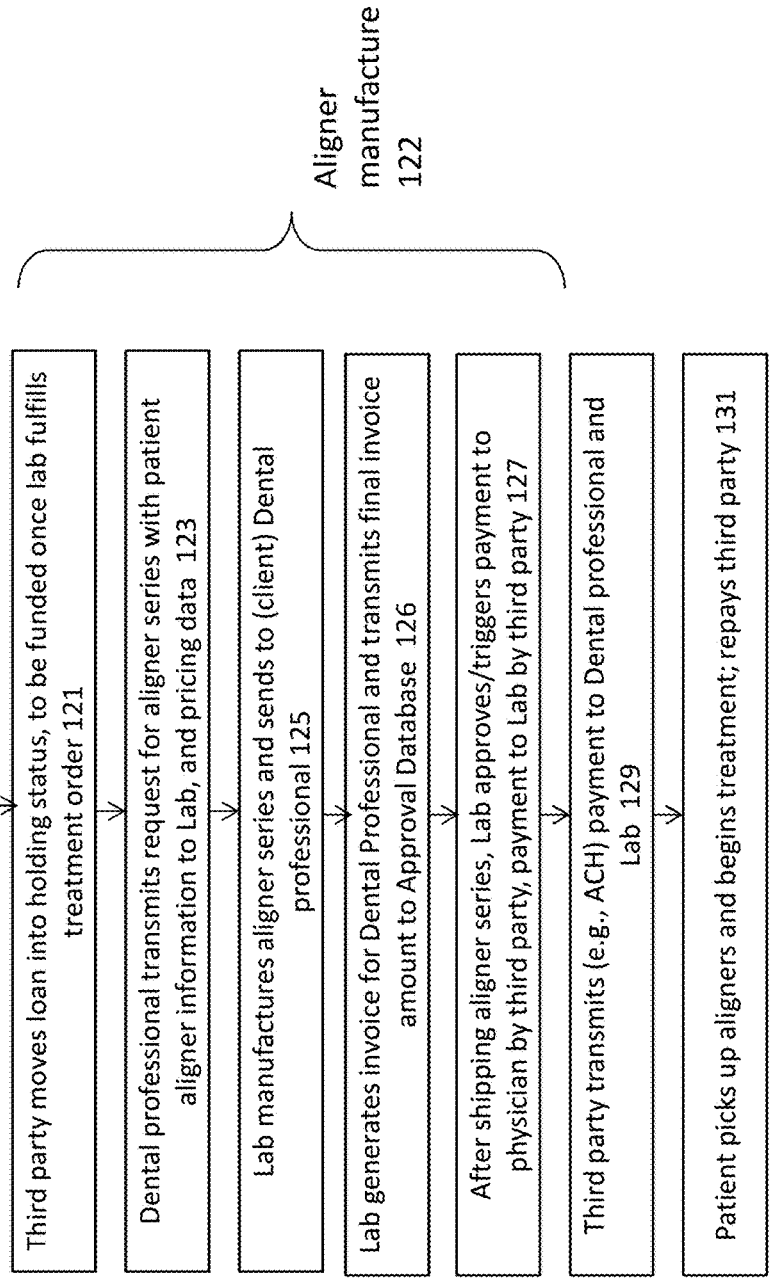
FIG. 1C is the second part of the diagram of FIG. 1B.

FIGS. 1B and 1C (shown across two pages) generally includes three or more periods. The first period is a pre-approval period. During this period, a patient (referred to herein as a "putative patient") that is interested in receiving treatment by a series of aligners expresses interest in financing the treatment 101. Prior to the methods and apparatuses described herein, this would likely involve the use of a third party financing service that could provide a loan which would be coordinated by the dental practitioner (e.g., dentist), and/or the dental practitioner may themselves provide financing. Instead, as shown in FIGS. 1B and 1C, the putative patient may be referred to a third party (third party financing service) to request preapproval. This process may be coordinated by the use of software, firmware and/or hardware, including software such as application software that is configured to run on a putative patient's own mobile device (e.g., smartphone). Thus, the putative patient may use a phone, tablet or other computer, including an app for the computing device (e.g., a mobile user interface) to request pre-approval for a phone, and provide the third party with patient identifying information 103. This may trigger the third party financial server either automatically or manually, or semi-automatically, to open a record of the patient (or update an existing record) in a database (e.g., a database of putative patient loan information, which may also be referred to as an approval database) 105.

Figures 3D, 3E:
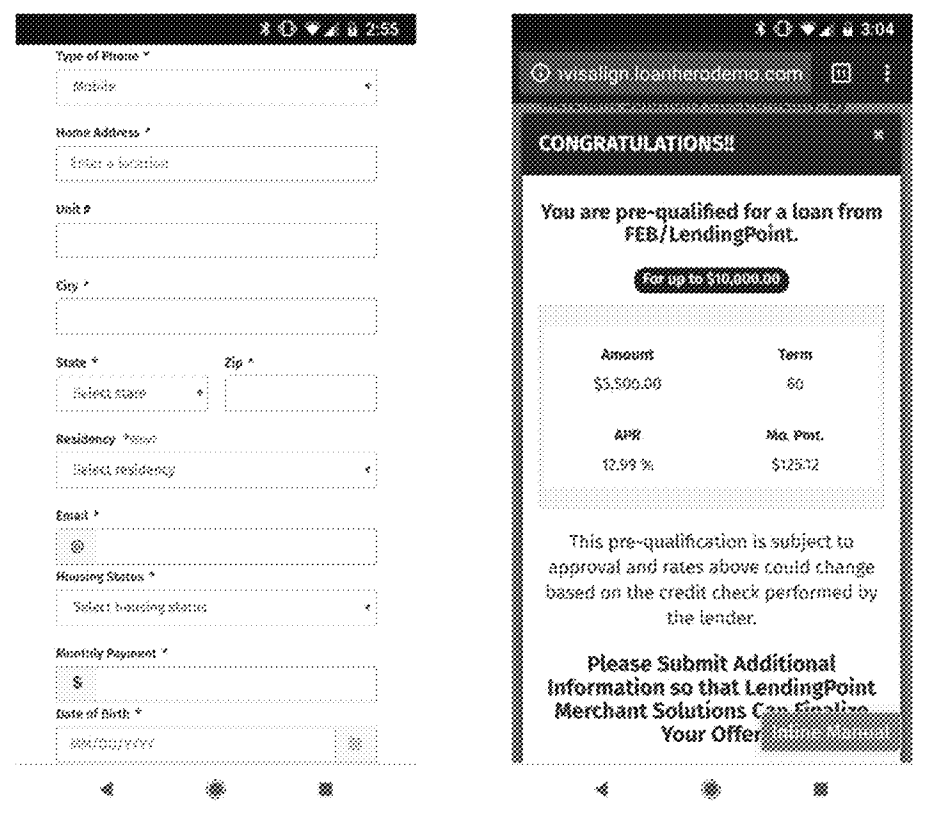

For example, FIGS. 3A1-3D illustrate an example of a user interface for requesting pre-approval for an aligner treatment, including manufacturing of the series of aligners. The putative patient may be sent (e.g., via SMS) a message requesting that they start the credit application, as shown in FIG. 3E. This message may provide a link that begins the credit application process, as shown in FIGS. 3A1 to 3B. The putative patient may enter their personal identifying information (name, social security number, phone number, address, date of birth/age, contact information, etc.), as shown in FIG. 3C-3D. This information may be submitted to the third party financing service which may update the database with this information, as well as the decision on the pre-approval inquiry. A notice indicating that the patient has been pre-qualified may be sent via the same channel, shown in FIG. 3E.

Returning to FIG. 1B, the dental aligner laboratory typically has "master" access to this database, which may be maintained by the dental aligner laboratory, or more likely by the third party financing service. The dental aligner laboratory may monitor, modify and/or receive alerts and/or updates from this database. In this case, opening or updating an entry specific to the potential user may trigger one or more alerts (e.g., notifications) to the dental aligner laboratory. Further, the third party financing service may make a decision to pre-approve or deny the prospective patient, and, if preapproved, may determine, initially based on the putative patient's credit (e.g., credit score, credit check, etc.) a maximum pre-approved amount. The third party may then update this database with approve/deny decision and approved amount, as mentioned 107.

Figure 10:
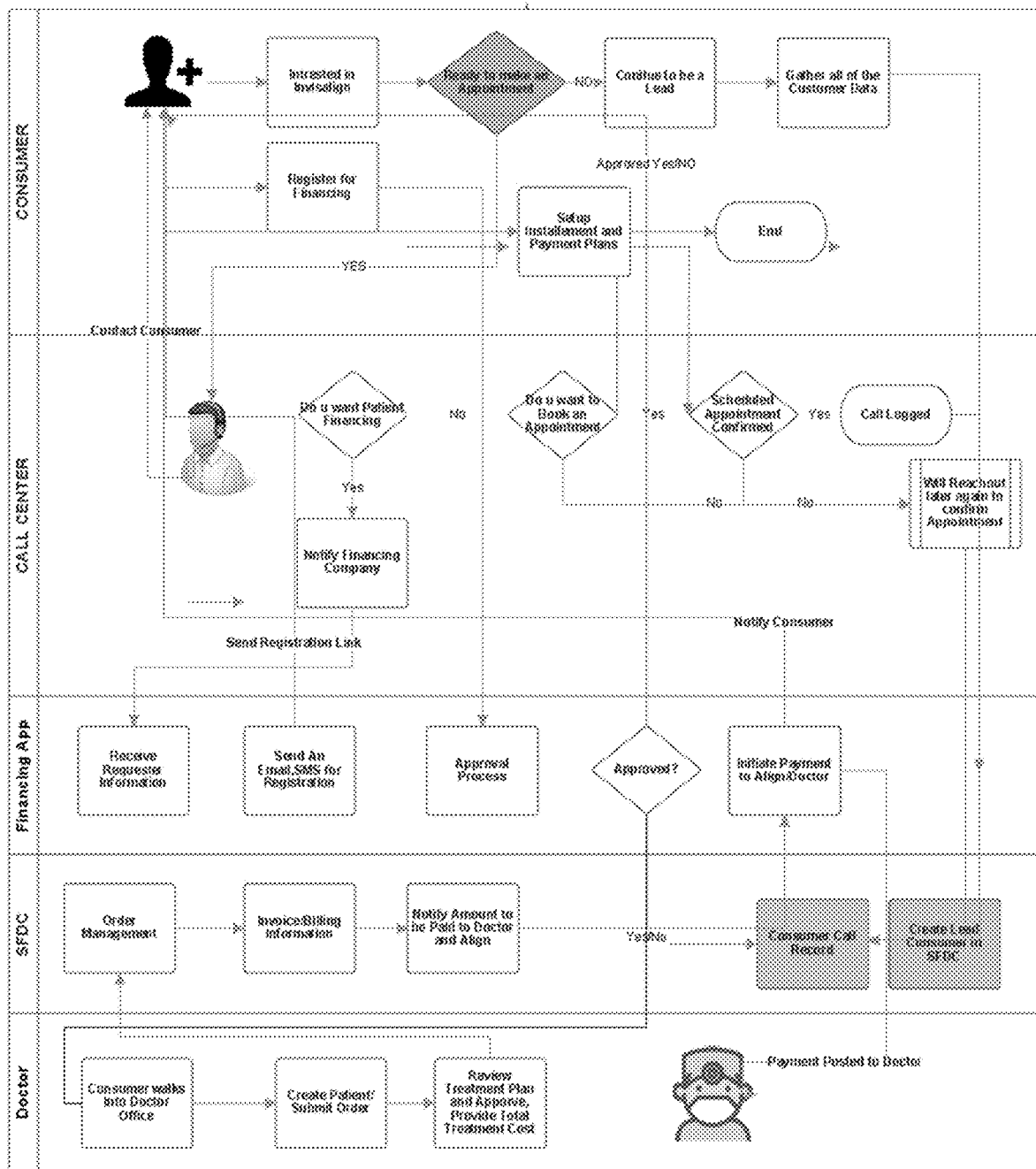
FIG. 10 is an alternative diagram illustrating a method of fabricating a series of aligners.

Note that the pre-approval period may occur either before or during a visit to a dental practitioner (e.g., orthodontist, dentist, etc.). As illustrated in FIG. 10, in some cases the putative patient may call into an information call center (e.g. consultant) affiliated with the dental aligner laboratory. The consultant may provide the link to the financial services or this may be provided while visiting/consulting with a dental practitioner.

A pre-treatment period may then enter the pre-approval period. The pre-treatment period may include the visit to the dental practitioner, who may examine the patient's teeth, including taking images, scans, etc. 109. This information may be provided to the dental aligner laboratory and may include the patient identifying information. This information may also be included in (or linked to) the database. The dental practitioner may then request preapproval information from either the dental aligner laboratory or directly (as a client account of the dental aligner laboratory) from the third party financing service 111. In some cases, the dental practitioner's records for the patient may be partially or completely reconciled (including filled in) by information from the database 113. Preapproval status (e.g., preapproved of ran amount of $X dollars") may be provided to the dental practitioner. In some case, this information may come through the laboratory 115, or it may alternatively come directly from the database. The dental practitioner may then provide treatment options (including various cost options 117) to the putative patient. If the patient agrees to the treatment, she or he may then select which treatment options and/or loan terms 119. Any of these methods may also include an initial down-payment.

Figure 5:
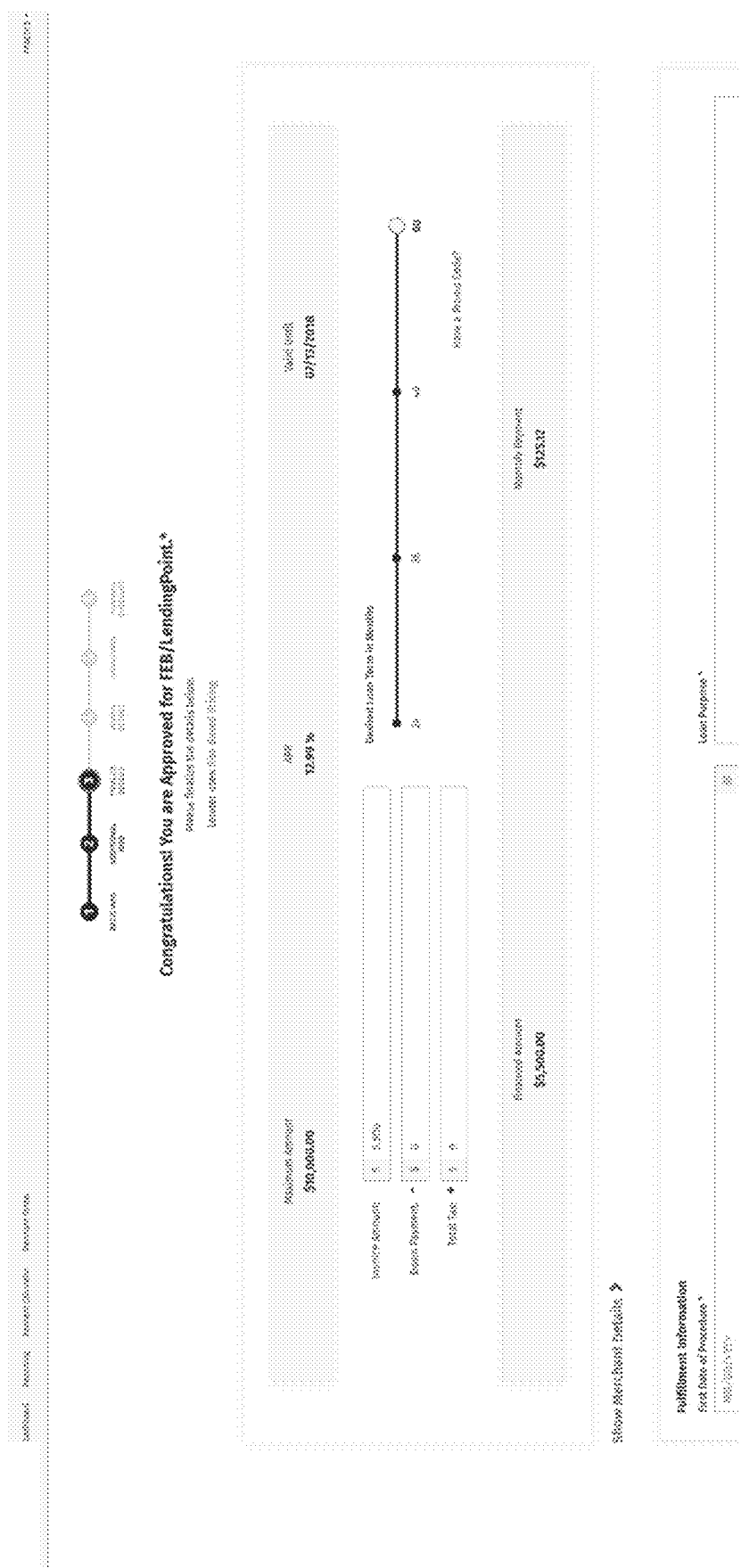
FIG. 5 illustrate an exemplary user interface that may be used to select and approve a treatment loan as described herein.

FIGS. 4A-4I illustrate one example of a user interface showing the selection of a finance plan (FIG. 4A), and the approval of the terms of the loan offered by the third party (FIGS. 4B-4D). The putative patient may then accept the loan, as shown in FIG. 4E, and set up a repayment plan (FIGS. 4F-4G). The loan may then be funded by the third party. FIG. 5 is another example of a user interface for communicating between the third party and the dental practitioner, allowing the dental practitioner to provide an estimate of the treatment cost and therefore different payment plans. This information (e.g., treatment cost) may be updated and sent to the database; receipt of the cost information from the dental practitioner may also trigger an alert and/or request for the laboratory cost from the dental aligner lab. The dental aligner lab may calculate the cost based on the presumptive treatment (e.g., based on patient dental information) and/or based on the identity of the dental practitioner and/or based on any promotional or discount programs. This cost (the laboratory fee) may then be transmitted and stored in the database.

Figure 9:
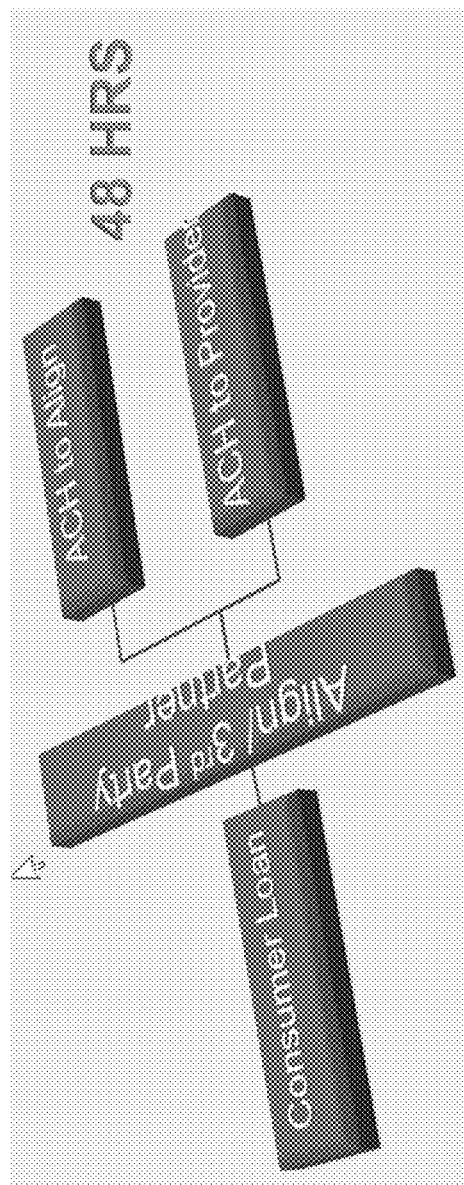
FIG. 9 is an illustration of the Third Party transmission (e.g., ACH) payment to Dental Professional and Lab following sending of aligner series to Dental Professional.

Returning to FIG. 1C, the aligner manufacture period 122 may update the database 121 and may include indicating (e.g. alerting) the dental aligner laboratory that the Third party moved loan is in holding status, to be funded once the lab fulfills treatment order. This may allow the laboratory (e.g., manufacturer) to prepare for processing of fabricating the series of aligners. For example, the dental practitioner may transmit the formal request for a series of aligners with patient aligner information to the laboratory. The laboratory may then manufacture the aligner series and send it to the dental practitioner 125. The lab may generate an invoice for Dental Professional and transmits final invoice amount to Approval Database 126. After manufacture and/or shipping the aligner series, the laboratory approve/triggers payment to physician by third party, as well as concurrent payment to Lab by third party 127. This is illustrated in FIG. 9. The third party transmits (e.g., ACH) payment to the dental practitioner and Laboratory 129, and the patient gets the aligners from the dental practitioner and beings treatment 131.

The methods described above may be modified by removing or minimizing the dental practitioner's role; including sending the aligners directly to the patient.

Figure 2A:
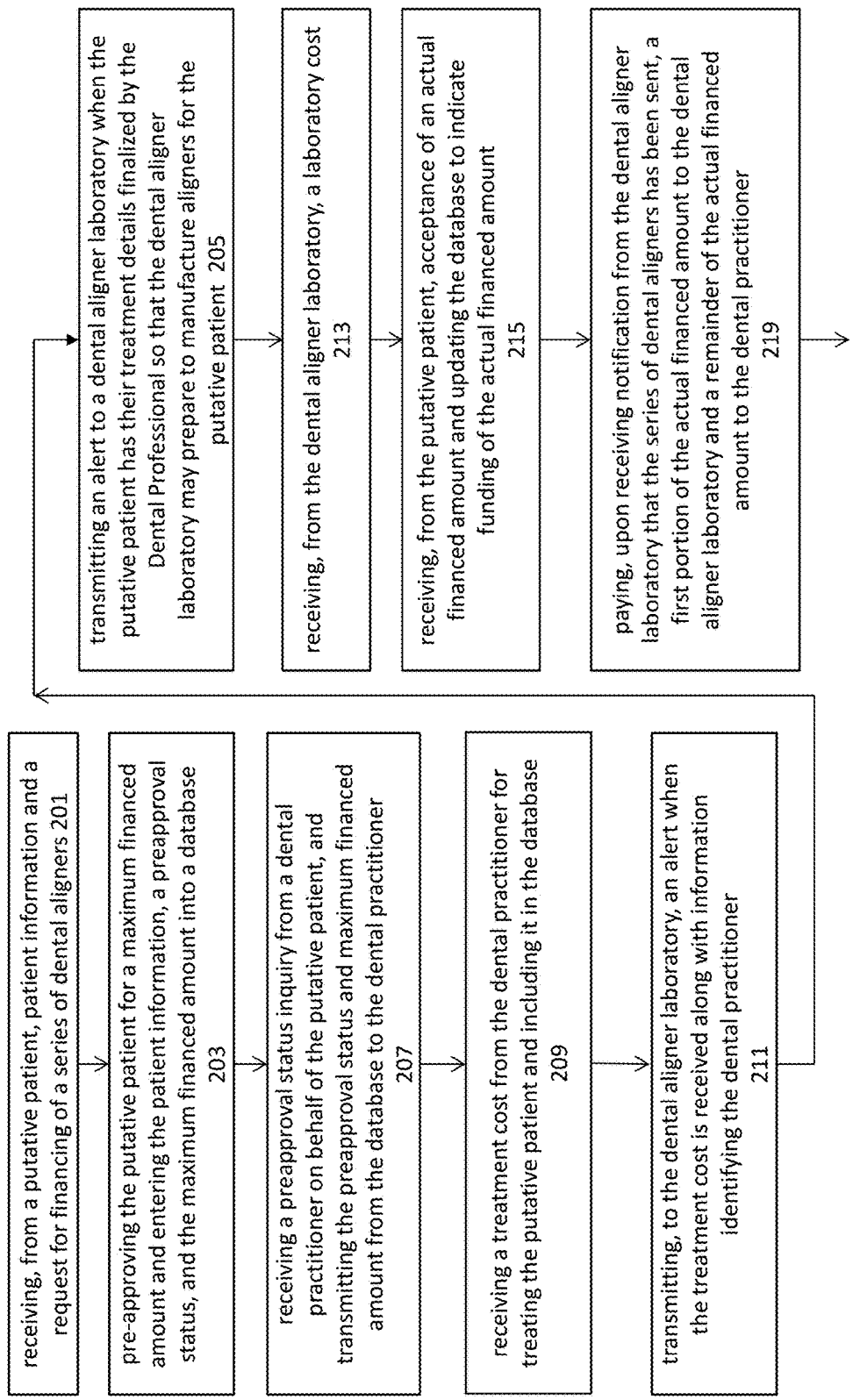
FIG. 2A illustrates one example of a method or fabricating a series of aligners from the perspective of the third party financing service.
Figure 2B:
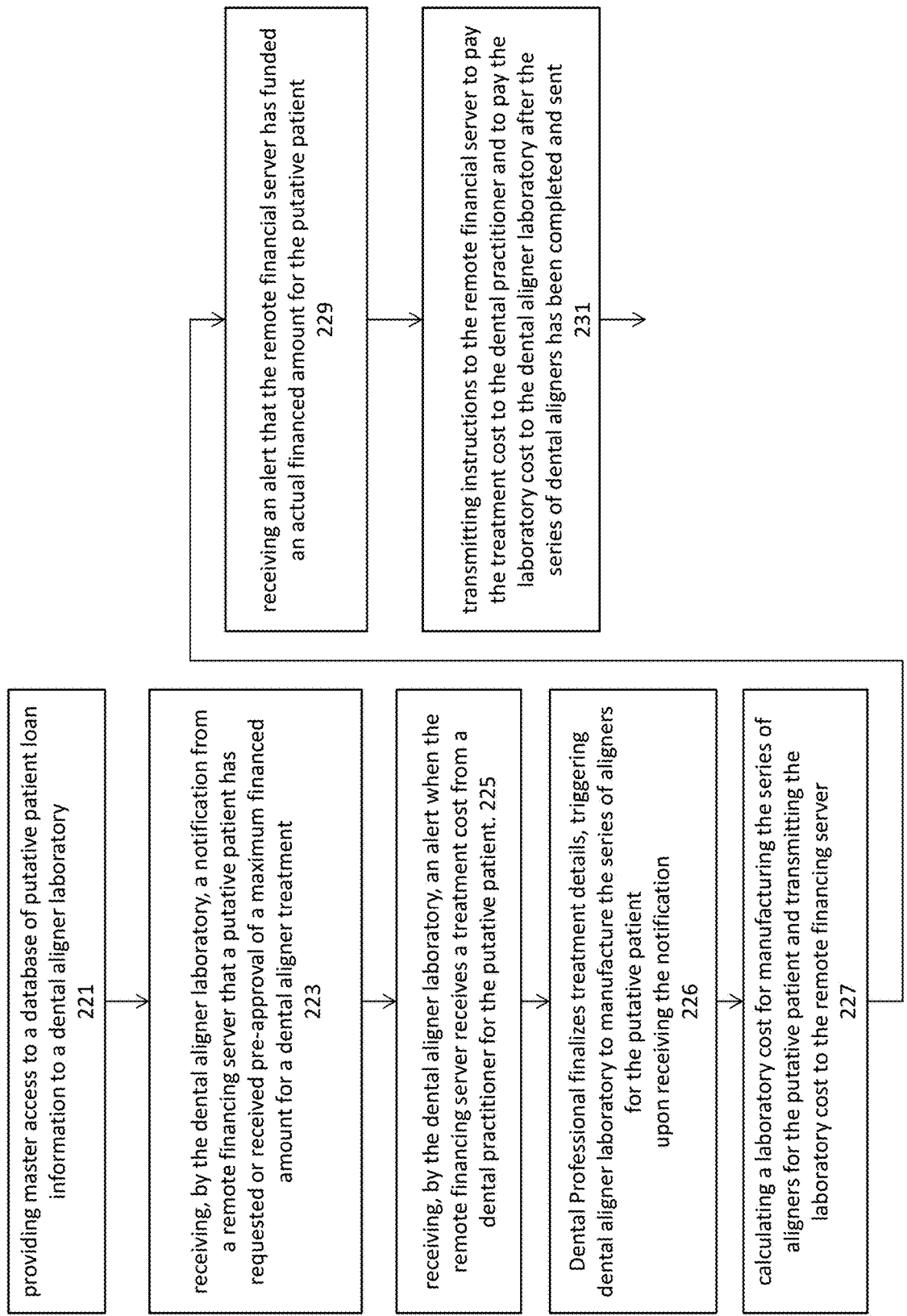
FIG. 2B illustrates and example of a method of fabricating a series of aligners from the perspective of a dental aligner laboratory (manufacturer).

FIGS. 2A and 2B illustrate methods similar to those discussed above.

For example, FIG. 2A illustrates a method of manufacturing a series of aligners that includes: receiving, from a putative patient, patient information and a request for financing of a series of dental aligners 201; pre-approving the putative patient for a maximum financed amount and entering the patient information, a preapproval status, and the maximum financed amount into a database 203; receiving a preapproval status inquiry from a dental practitioner on behalf of the putative patient, and transmitting the preapproval status and maximum financed amount from the database to the dental practitioner 207; receiving a treatment cost from the dental practitioner for treating the putative patient and including it in the database 209; transmitting, to the dental aligner laboratory, an alert when the treatment cost is received along with information identifying the dental practitioner 211; transmitting an alert to a dental aligner laboratory when the putative patient has their treatment details finalized by the Dental Professional so that the dental aligner laboratory may prepare to manufacture aligners for the putative patient (optional step 205); receiving, from the dental aligner laboratory, a laboratory cost 213; receiving, from the putative patient, acceptance of an actual financed amount and updating the database to indicate funding of the actual financed amount 215; in some variations, the dental aligner laboratory may receive an alert that the database has been updated to indicate funding of the actual financed amount so that the dental aligner laboratory may manufacture the series of aligners; and paying, upon receiving notification from the dental aligner laboratory that the series of dental aligners has been sent, a first portion of the actual financed amount to the dental aligner laboratory and a second portion (e.g., a remainder) of the actual financed amount to the dental practitioner 219.

Thus, in any of the method and system variations described herein, the dental aligner laboratory may be alerted early in the process and may therefore make preliminary preparations for treatment, including assisting the dental practitioner in identifying a treatment product, scheduling of treatment processing, etc. For example, the laboratory may assist in identifying a treatment product by providing directly the practitioner or to the database a listing and/or description of dental aligner products (e.g., treatments using a limited or pre-defined number of aligners or for limited time duration (8 months, one year, 1.5 years, etc.), treatments using/not using attachments to the teeth in addition to aligners, treatments focused on primarily aesthetics, etc.

For example, any of these methods may include transmitting an alert to the dental aligner laboratory when the putative patient is pre-approved so that the dental aligner laboratory may prepare to manufacture aligners for the putative patient. Preparation may include scheduling aligner manufacturing resources, communication with the database, patient and/or dental practitioner about available treatment plan options, opening and/or populating a local patient treatment record, or the like.

FIG. 2B describes a method of manufacturing a series of dental aligners that includes: providing master access to a database of putative patient loan information to a dental aligner laboratory 221; receiving, by the dental aligner laboratory, a notification from a remote financing server that a putative patient has requested or received pre-approval of a maximum financed amount for a dental aligner treatment and (optionally) preparing to manufacture the series of aligners for the putative patient upon receiving the notification (optional) 223; receiving, by the dental aligner laboratory, an alert when the remote financing server receives a treatment cost from a dental practitioner for the putative patient 225; Dental Professional finalizes treatment details, triggering dental aligner laboratory to manufacture the series of aligners for the putative patient upon receiving the notification 226; calculating a laboratory cost for manufacturing the series of aligners for the putative patient and transmitting the laboratory cost to the remote financing server 227; receiving an alert that the remote financial server has funded an actual financed amount for the putative patient 229 and thereafter initiating manufacture of the series of dental aligners specific to the putative patient; and transmitting instructions to the remote financial server to pay the treatment cost to the dental practitioner and to pay the laboratory cost to the dental aligner laboratory after the series of dental aligners has been completed and sent 231.

Figure 6:
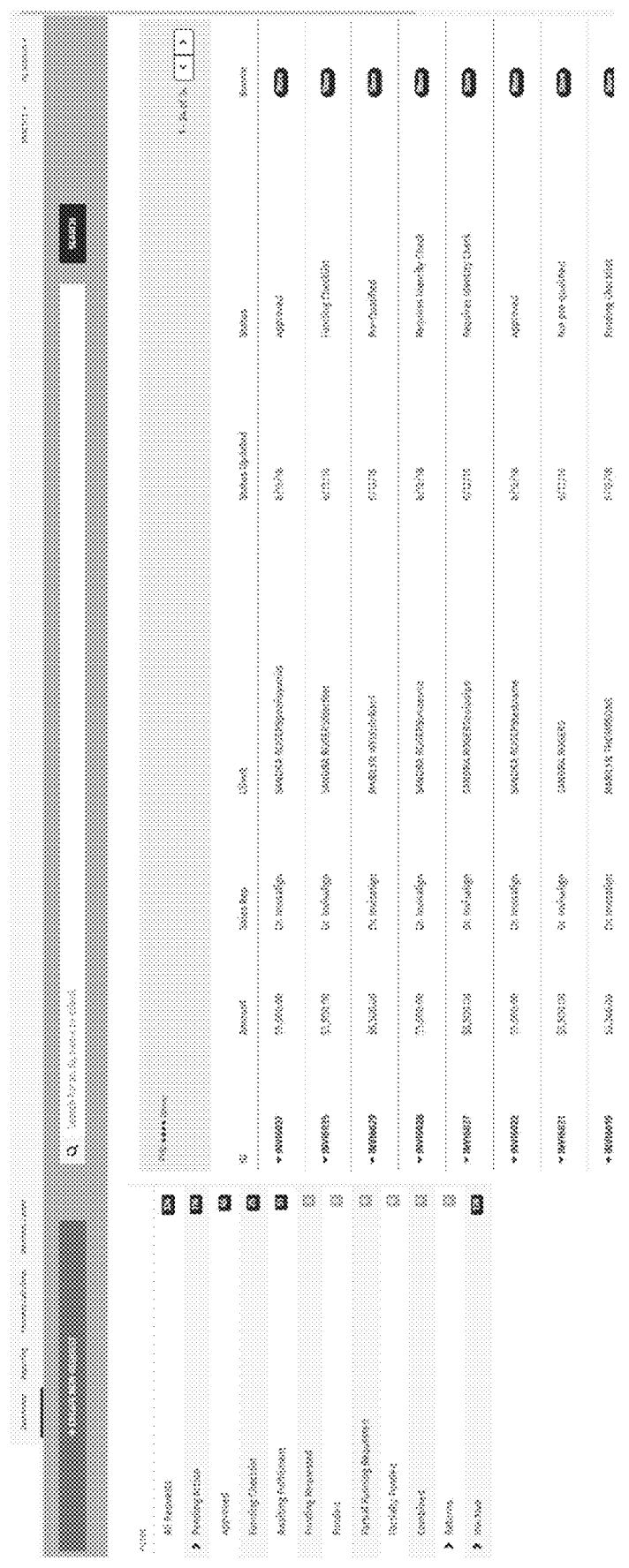
Figure 7:
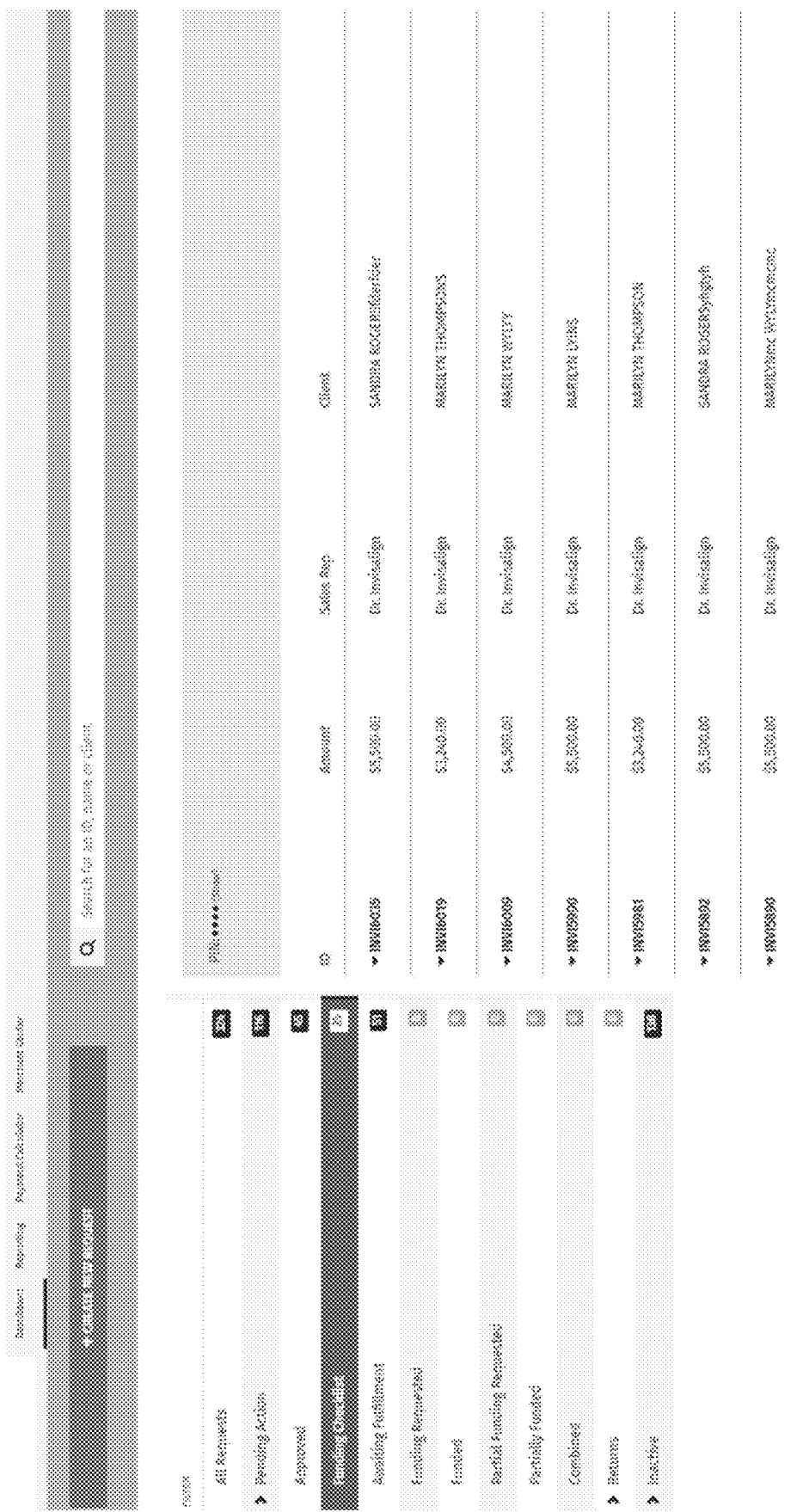
FIG. 7 is an example of a user interface for monitoring funding of loan from Approval Database by Master (e.g., Lab).
Figure 8:
FIG. 8 is an example of a user interface for a client (e.g., Dental Physician) of Master account (e.g., Lab).

FIGS. 6, 7 and 8 show user interfaces for communicating with the financial server, e.g., that may be used by the laboratory and/or dental practitioner to monitor the loan status and/or treatment status of one or more patients.

As mentioned, a patient interested in aligner therapy may initial contact the laboratory, e.g., by visiting a website or calling a call-in center, and may receive information about financing. An email or text message (based on patient preference) may be sent to allow the patient to enter information. This process may be done in real-time, indicating pre-approved or denies status. Once the patient approves of the loan documents, the loan may be funded. In the remote server (e.g., cloud), the funded loan status may be viewed by the laboratory. The laboratory system may look daily at loans funded and cross-reference them against the pipeline report of when the aligner series ships and leaves the manufacturer. The laboratory may alert the financing server that the aligners have shipped, thereby automatically telling the loan server (software) to pay the physician and to pay laboratory.

Figure 1D:
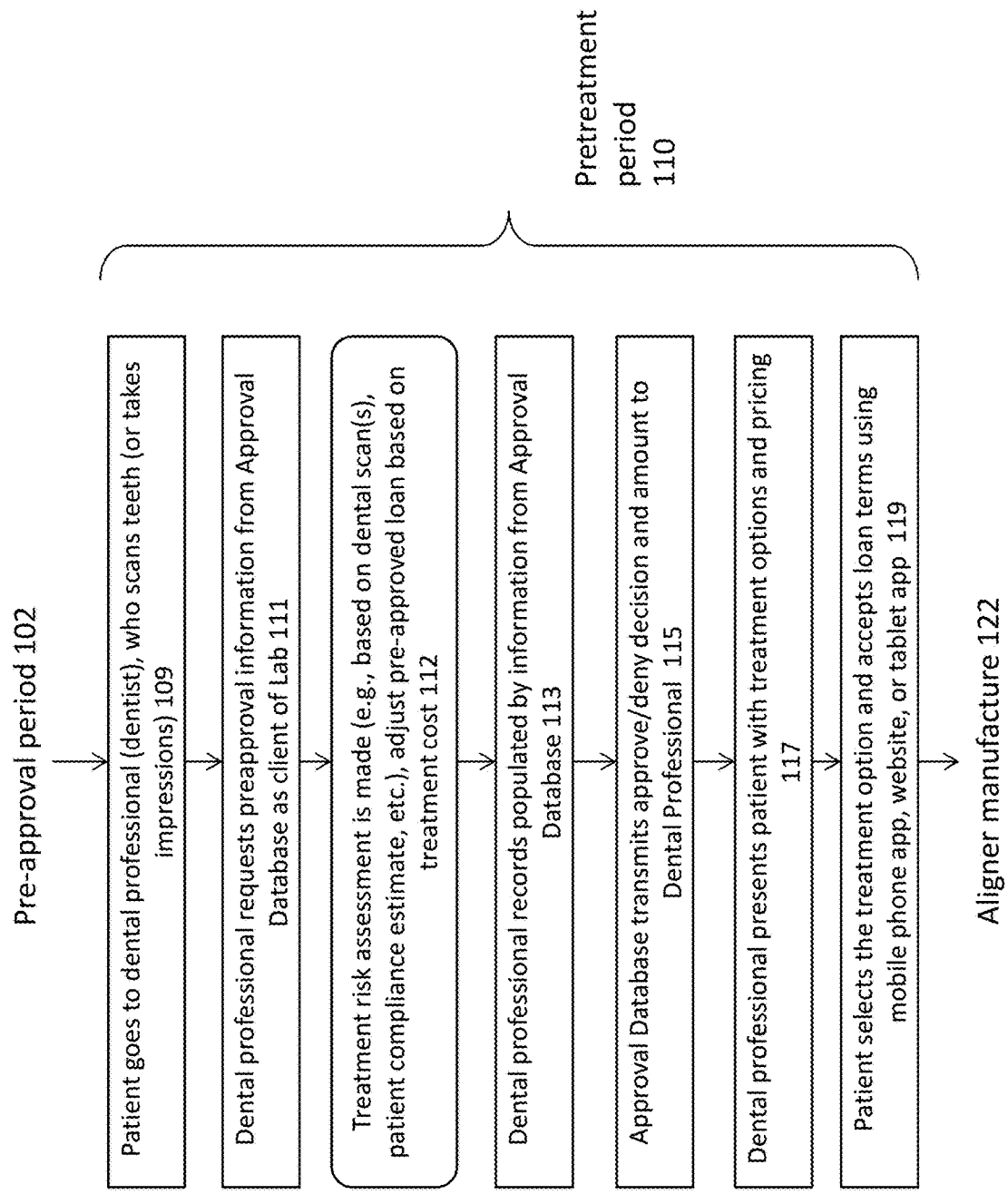
FIG. 1D is a flow diagram similar to that shown in FIGS. 1B-1C including one or more additional steps.

FIG. 1D illustrates one example of a variation in which the maximum loan amount could be modified based on dental information. For example, the loan amount could be modified based on predicted treatment outcome specific to the patient. Alternatively or additionally, the loan amount could be modified based on the predicted patient compliance. More complicated procedures could be approved for larger loan amounts, which may be drawn against in the future.

Figure 11:
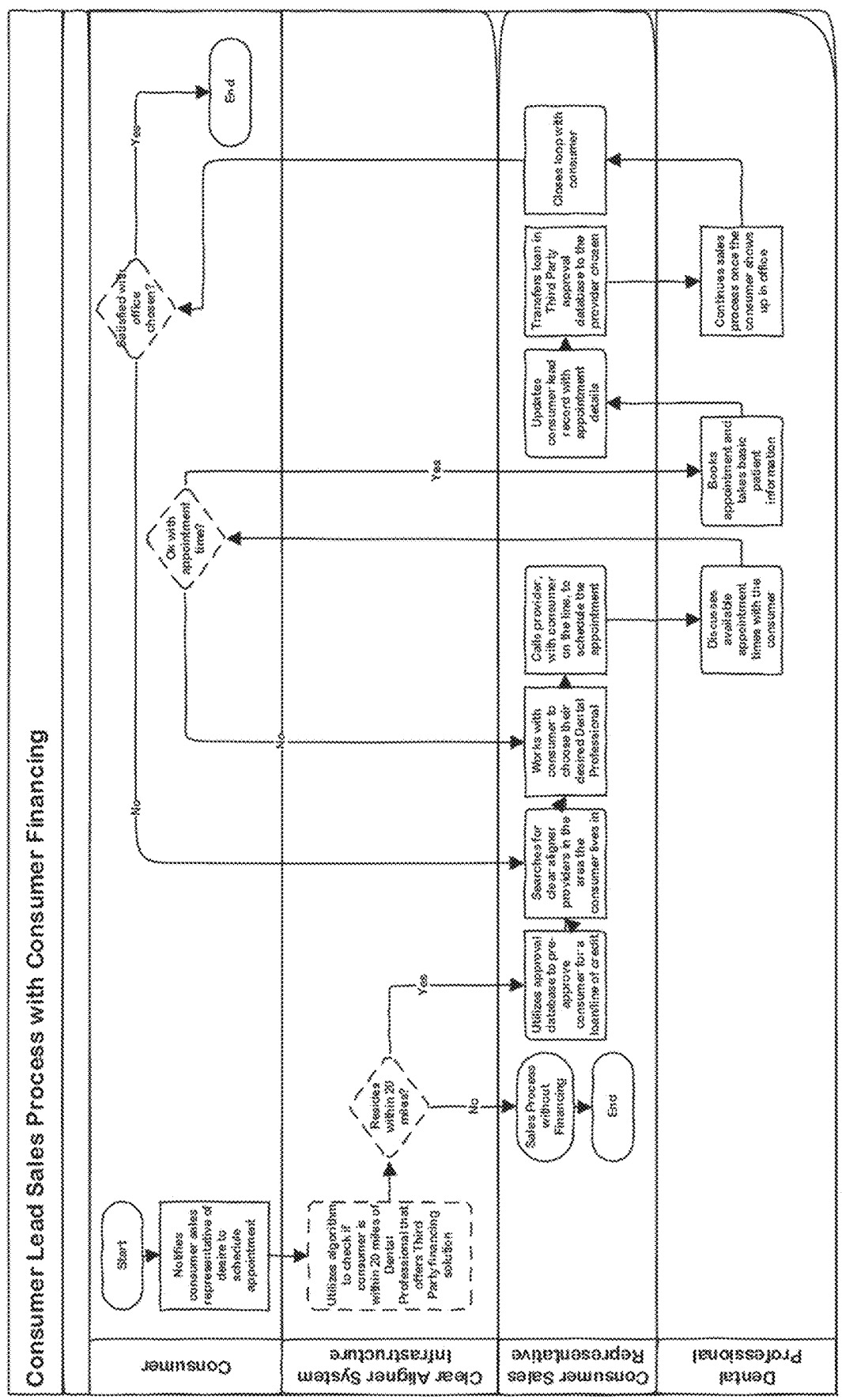
FIG. 11 schematically illustrates an example of a process flow for consumer sales including financing.
Figure 12:
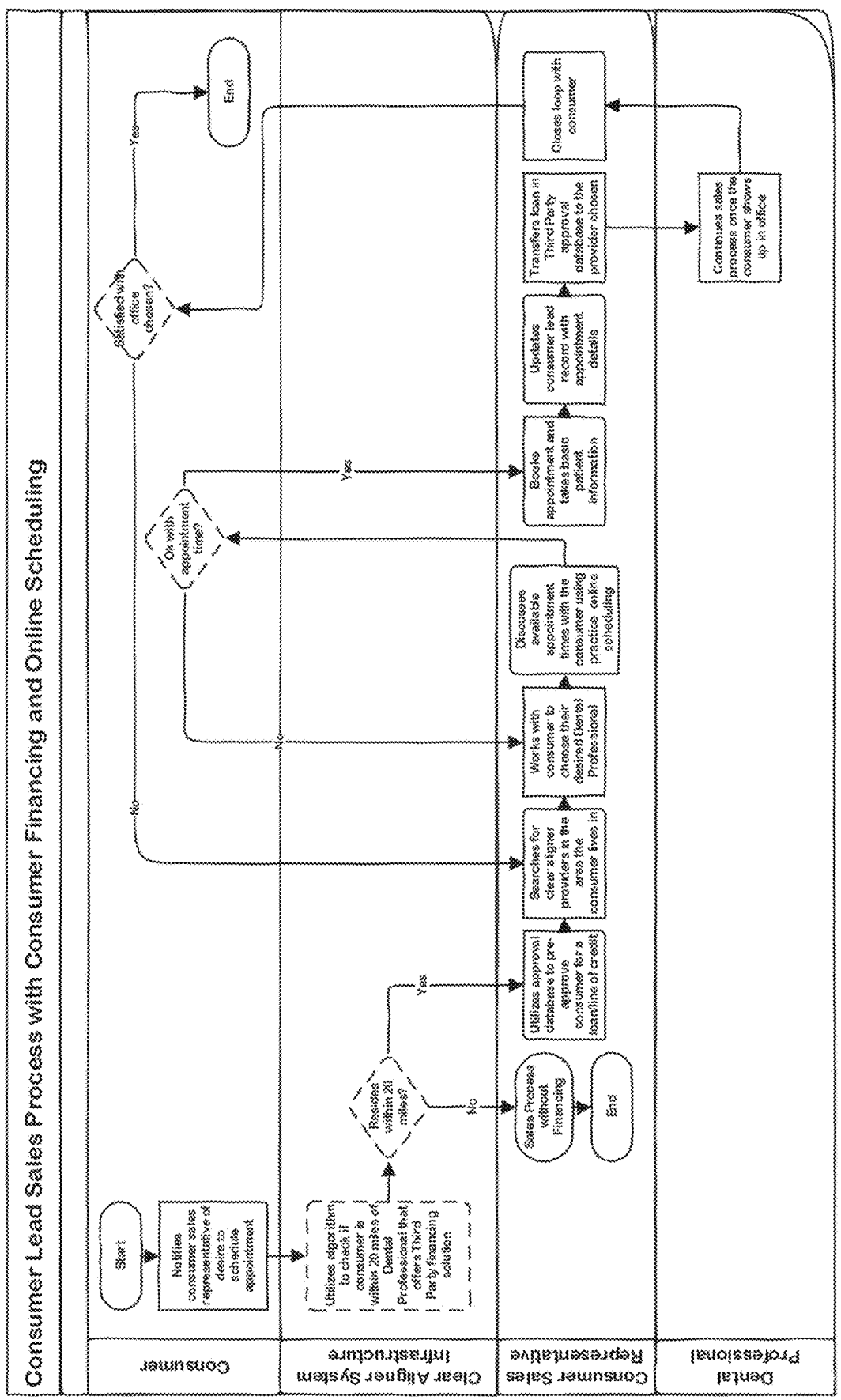
FIG. 12 schematically illustrates an example of a process flow for consumer sales including financing using online scheduling.
Figures 13A, 13B:
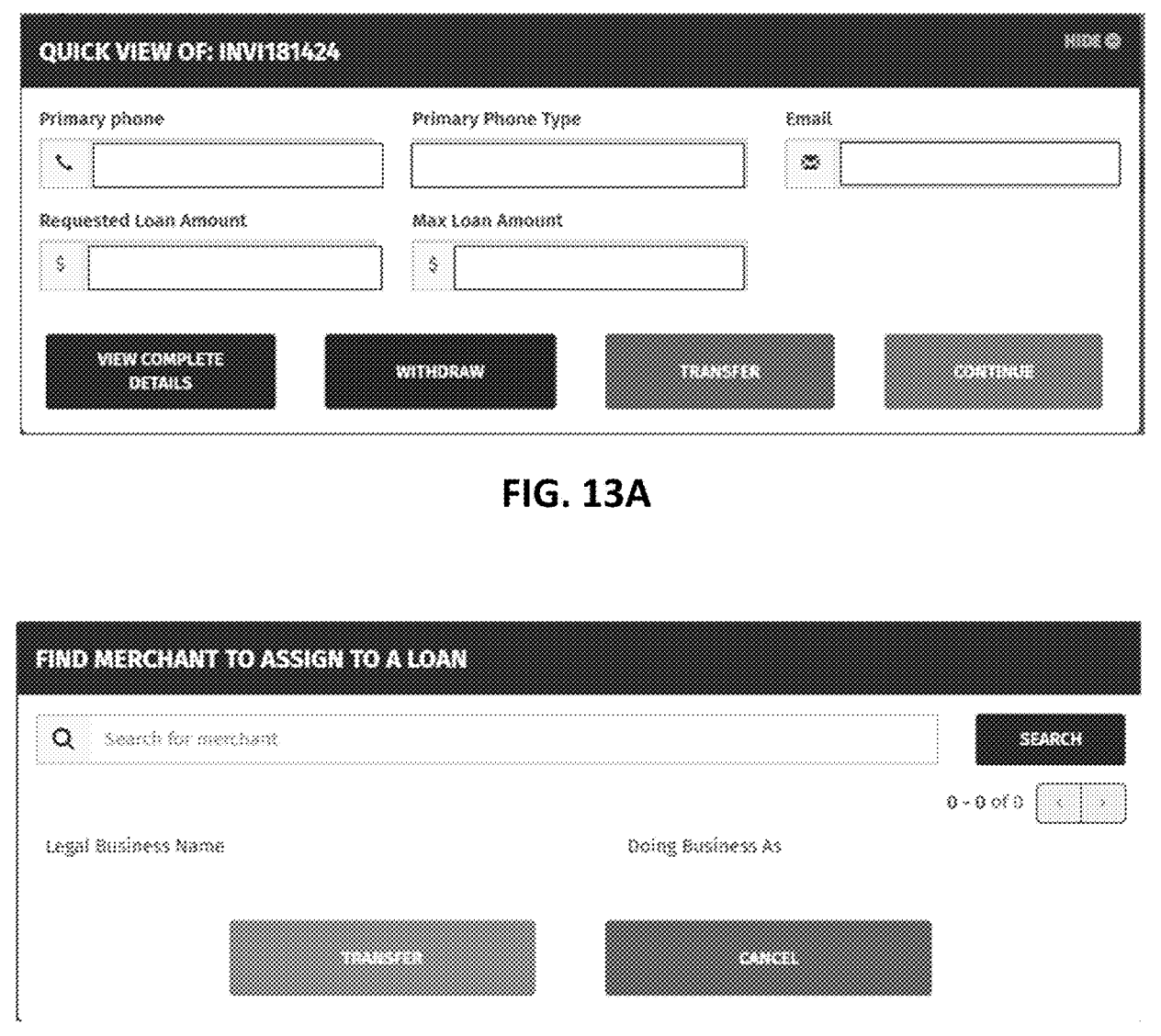

FIGS. 11 and 12 illustrate examples of process flows for recruiting customers (e.g., financing), including both with (FIG. 12) and without (FIG. 11) an online scheduling technique. In FIG. 11, the patient a consumer sales representative may manually book an appointment and walk the patient through some basic information both about the loan (e.g., explaining the significance of terms for the consumer loan and/or scheduling and aiding in securing the loan for a particular orthodontic product. FIG. 12 is an improvement on this manual method that includes the use of an automated (e.g., a smartphone owned or loaned to the patient, where the "smartphone" may be any hand-held electronic device including a processor). The smartphone application software may be used to provide information to user (patient) about aligner providers, e.g., physicians, etc. (including answering questions about provider practice, availability, etc.), and may aid in automatically scheduling an initial and follow-up appointments the provider, and/or may book appointment. The app/software may also act, as described above, to perform the loan approval process. FIGS. 13A and 13B illustrate examples of user interfaces for the application software when setting up and applying for a loan and/or treatment. FIG. 13A illustrates a user interface for displaying information about the patient and patient loan, such as user-identifying information (phone number, phone type, email, etc.), as well as the requested loan amount and the maximum loan amount. FIG. 13B illustrates a user interface for finding a merchant to assign to a loan.

Figure 14:
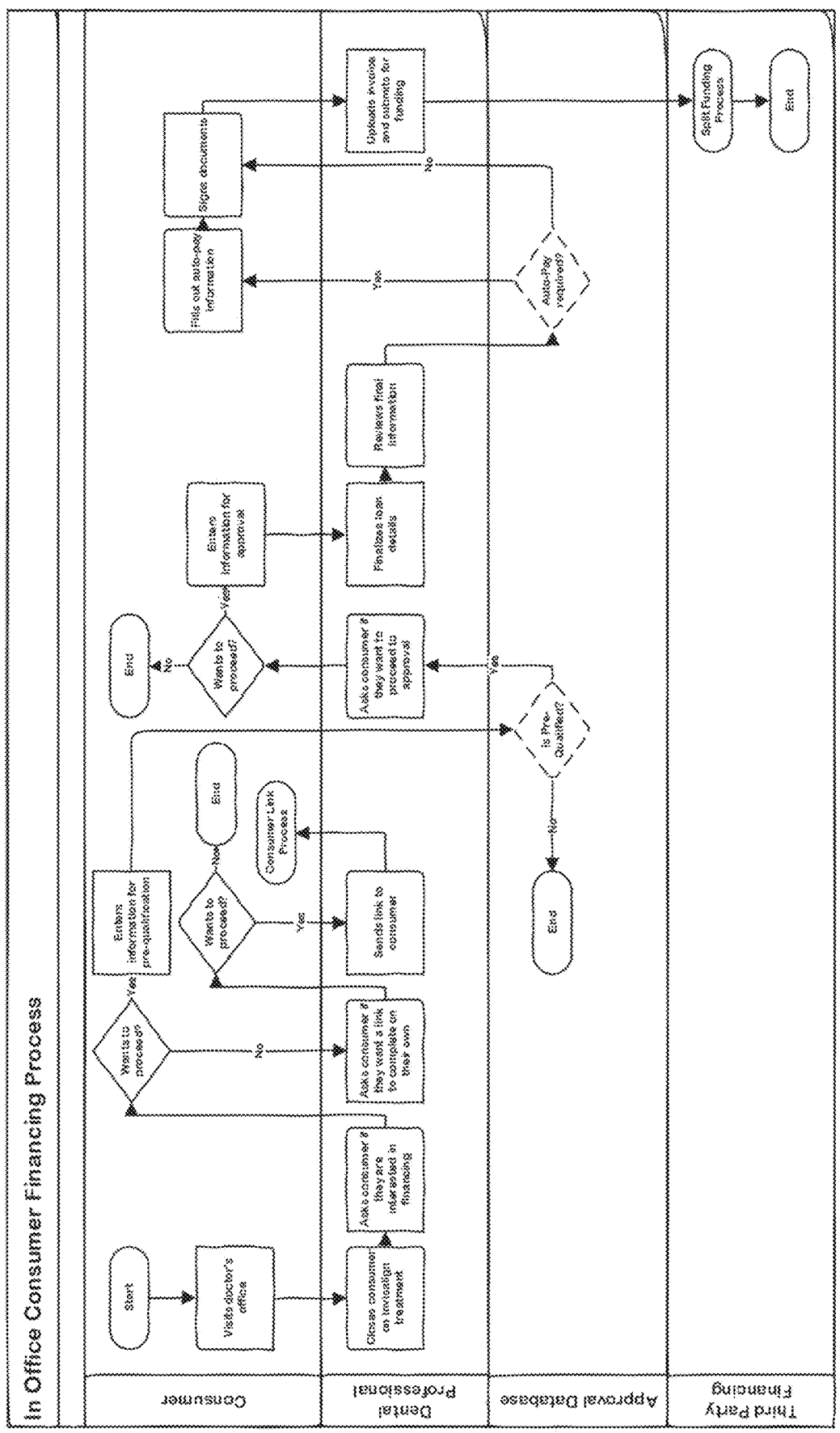
FIG. 14 is an example of an in-office consumer financing process.
Figure 15A:
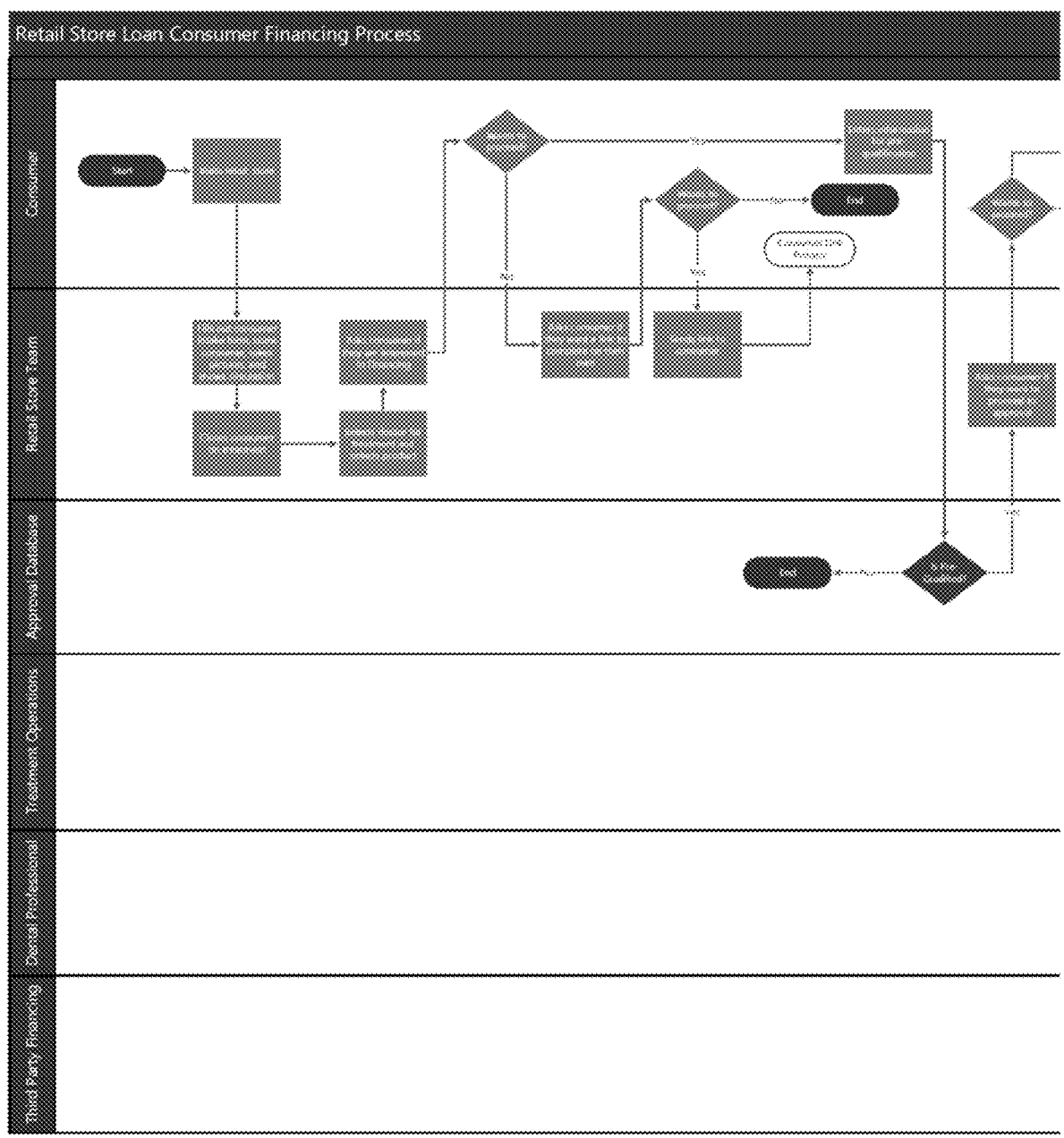
FIGS. 15A, 15B and 15C show a process flow diagram illustrating one example of a retail store loan consumer financing process example. The chart shown in FIG. 15A is continued onto FIGS. 15B and 15C.
Figure 15B:
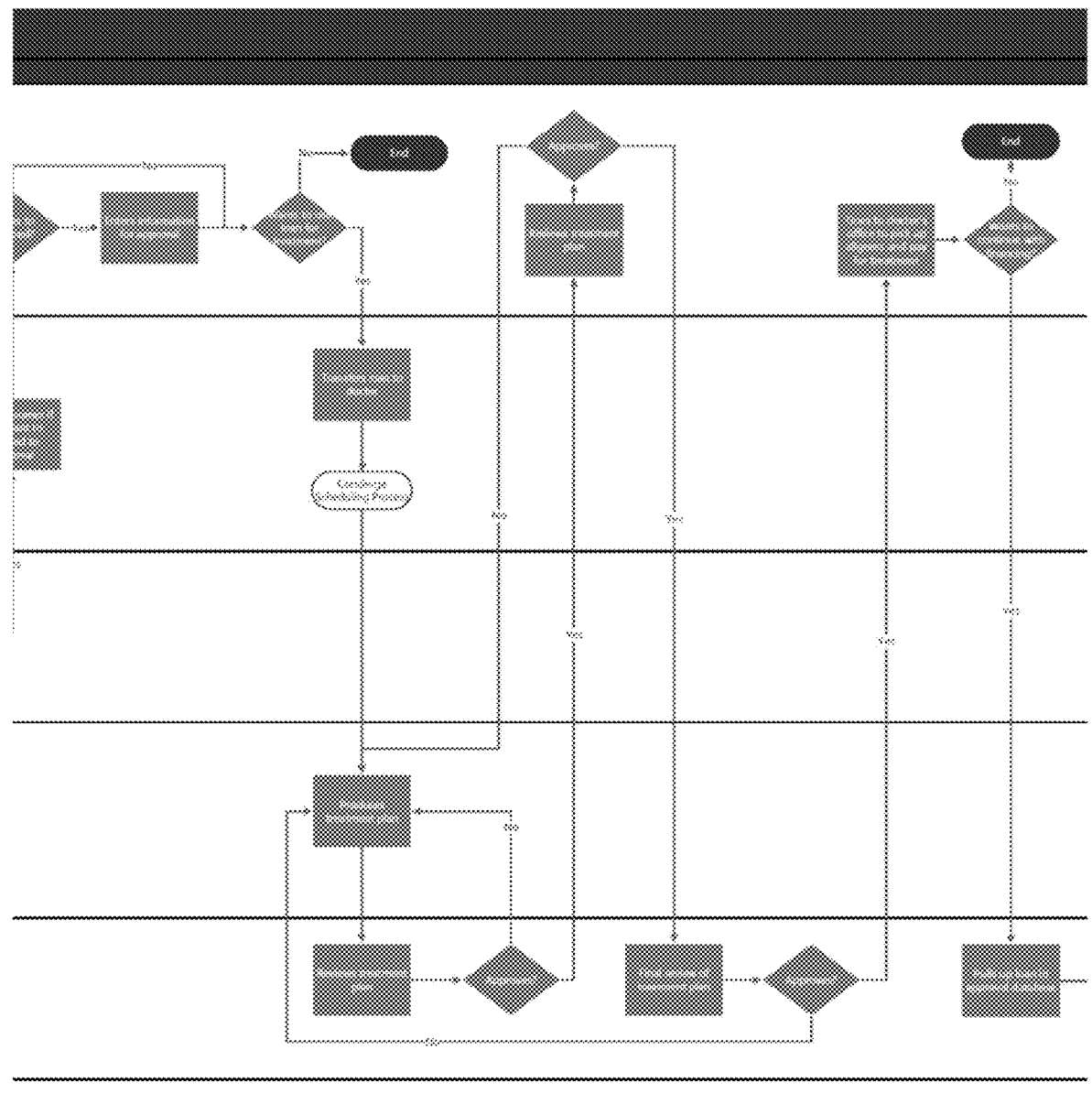
Figure 15C:
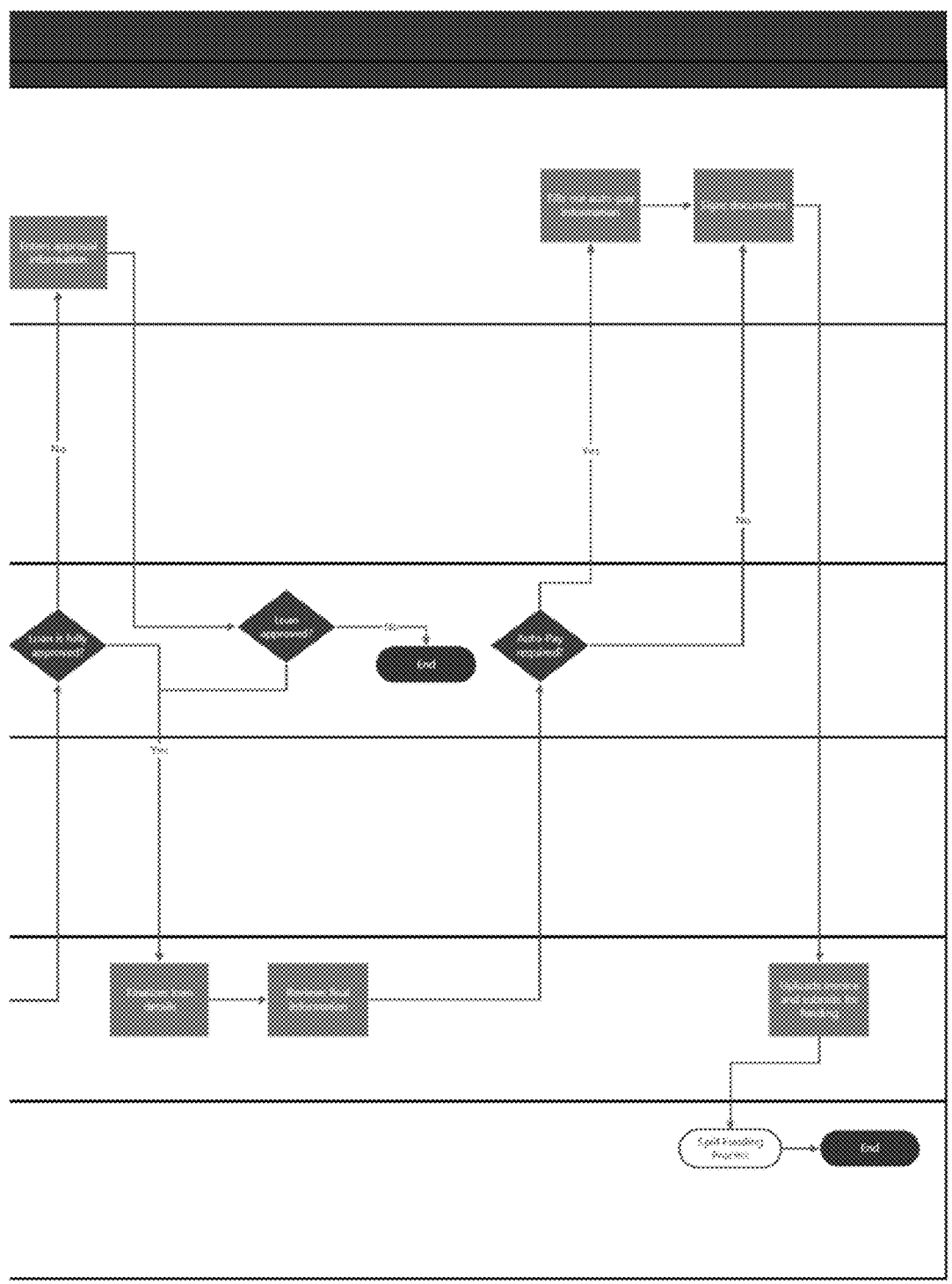
Figure 16A:
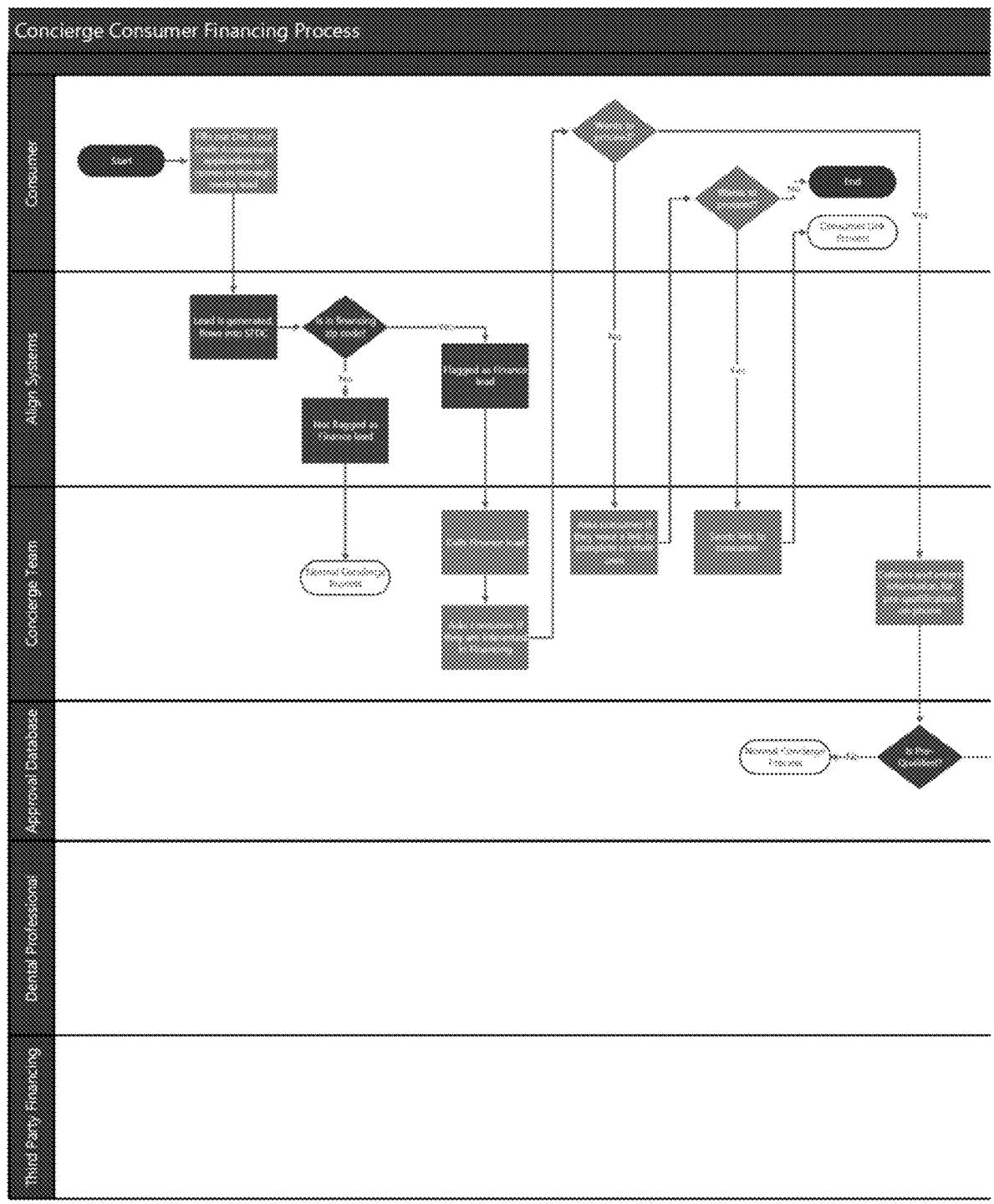
FIGS. 16A, 16B and 16C show a process flow diagram illustrating one example of a concierge consumer financing process. The chart shown in FIG. 16A is continued onto FIGS. 16B and 16C.
Figure 16B:
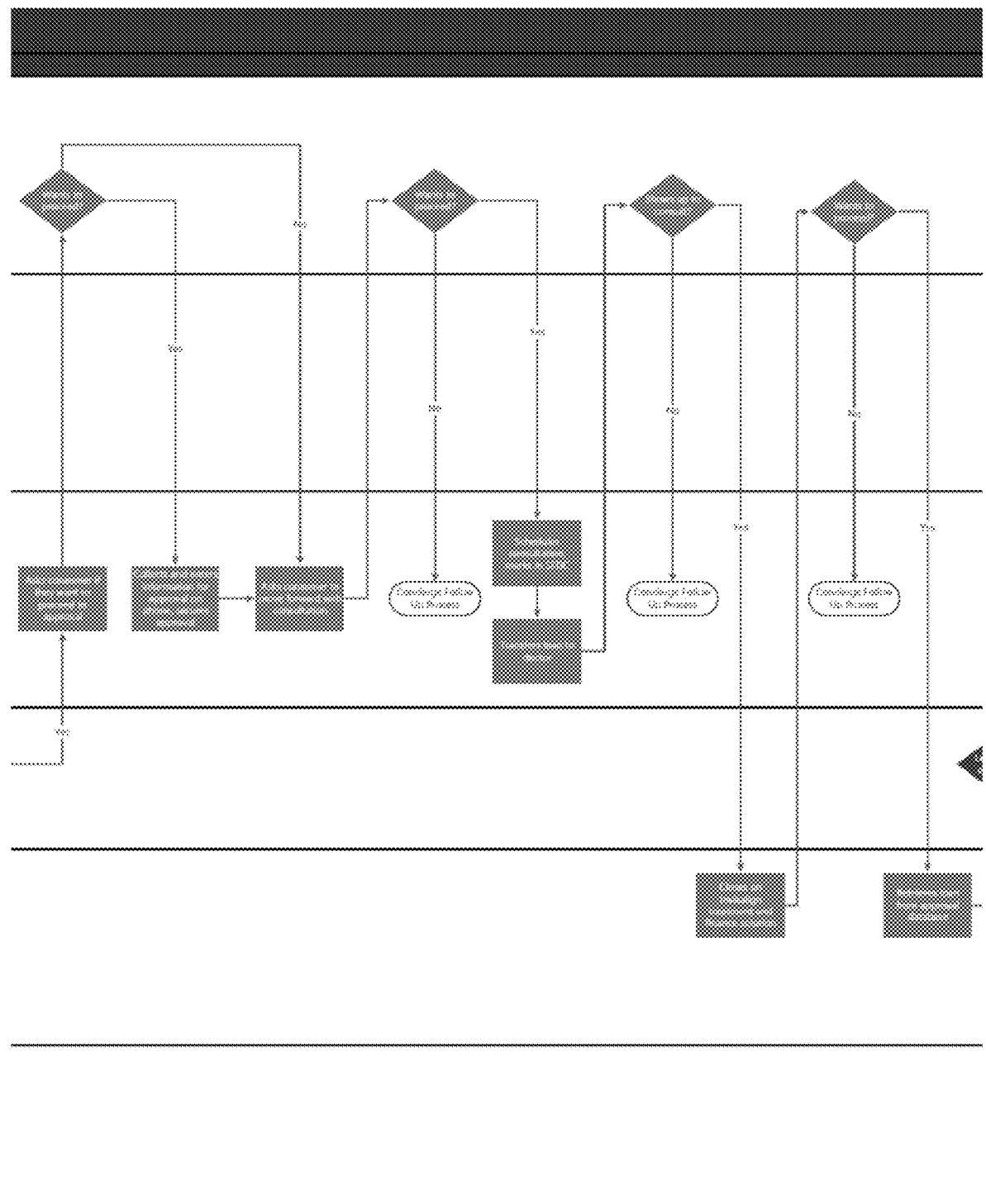
Figure 16C:
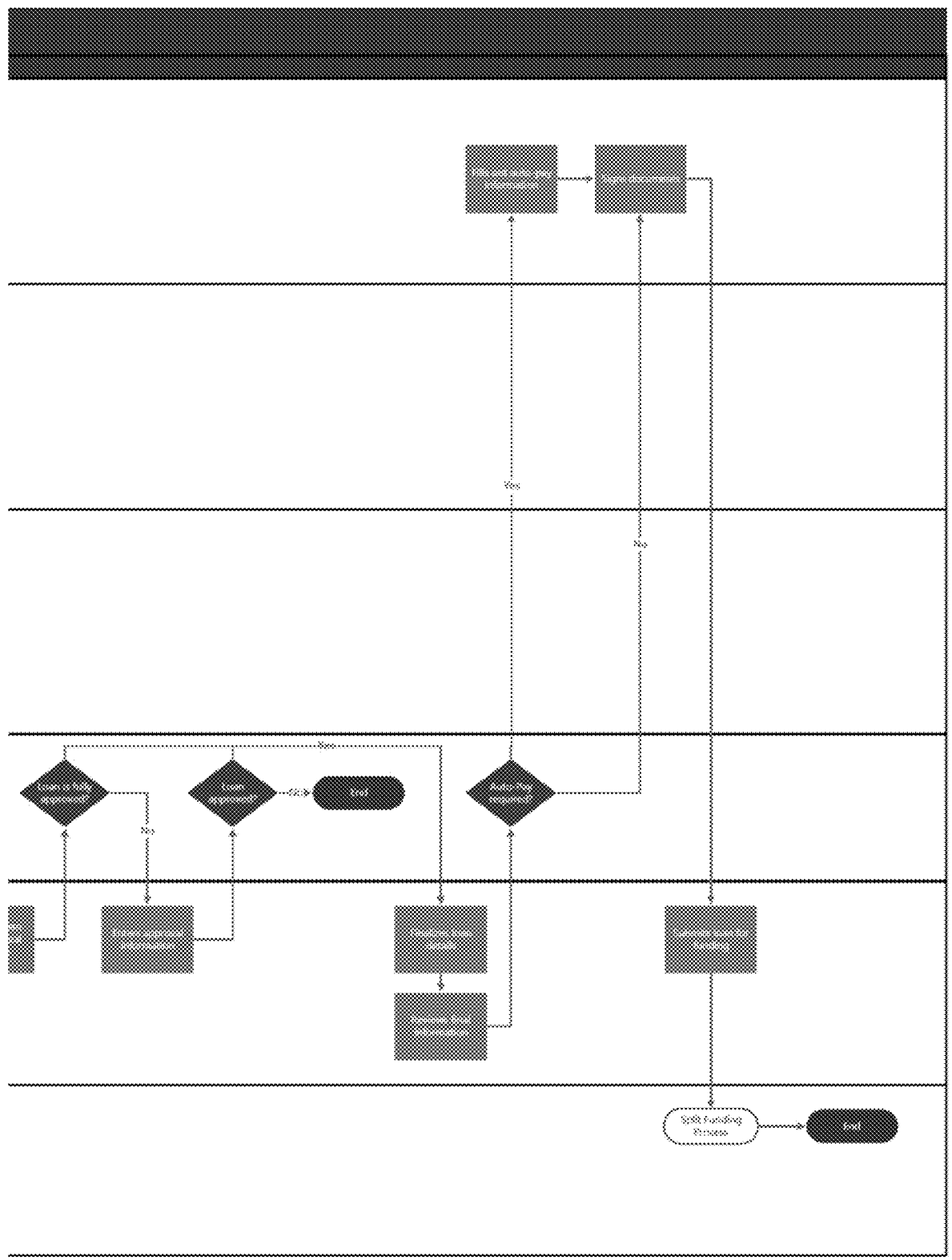

FIG. 14 illustrates one example of a method (shown as a process chart) for consumer financing and manufacturing of a patient orthodontic treatment including a plurality of aligners. FIGS. 15A-15C and 16A-16C illustrate process diagrams for retail store locations consumer financing processes and patient concierge consumer financing.

As discussed above in relation to FIGS. 1B-1C and 1D, the process of manufacturing aligners may be greatly improved by integrating the aligner manufacturing process with the consumer financing in a particular ordered manner. This may avoid the inefficiencies associated with waiting times, and the order of manufacturing operations. Prior systems required the dental provider (e.g., orthodontist, dentist, etc.) to bear the burden of coordinating the patient loan and, setting up a treatment plan and ordering the aligner(s). The methods and systems described herein may address these inefficiencies, by integrating the dental laboratory in the loan process, including transmitting an alert to the dental aligner laboratory when the putative patient is pre-approved so that the dental aligner laboratory may begin to prepare to manufacture aligners for the putative patient and transmitting an alert to the dental aligner laboratory when the treatment cost is received from the dental practitioner, along with information identifying the dental practitioner, and finally, transmitting an alert to the dental aligner laboratory that the database has been updated to indicate funding of the actual financed amount so that the dental aligner laboratory may manufacture the series of aligners.

In practice, these processes may be aided by the use of both a patient processor (e.g., a smartphone, tablet, etc.) near the patient that may provide information to the patient, including a user interface such as shown in FIGS. 3A1-3E and 4A-4I, which may communicate with a third party processor (e.g., a remote processor) and may also directly or indirectly communicate with a dental practitioner (dentist, orthodontist, etc.) processing device (e.g., client processor, such as a computer, tablet, etc.) and/or laboratory processing device (e.g., master processor, such as a computer, tablet, etc.).

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method using a system that includes a financing server in communication with a putative patient, a dental appliance laboratory and a dental practitioner, the method comprising:
   updating a database of the financing server to indicate that the putative patient is pre-approved for a treatment loan;
   establishing, by the financing server, different levels of access to the database for the dental appliance laboratory and the dental practitioner, wherein master access to the database is provided to the dental appliance laboratory, and client access to the database is provided to the dental practitioner, wherein the master access provides the dental appliance laboratory with an ability to monitor the database by receiving alerts from the financing server regarding different stages of the putative patient's financing;

receiving, from the dental practitioner, a treatment cost representing a cost of the dental practitioner to implement a treatment plan for treating the putative patient's dentition using a series of dental appliances;

providing, to the dental appliance laboratory, a first alert indicating that the treatment cost from the dental practitioner was received by the financing server;

receiving, from the dental practitioner or the putative patient, an acceptance of a specific financing option;

providing, to the dental appliance laboratory, a second alert indicating that funding for an actual financed amount for the putative patient has been received; and triggering payment to the dental practitioner and the dental appliance laboratory in response to receiving an indication from dental appliance laboratory that a treatment order has been fulfilled.

2. The method of claim 1, wherein the one or more financing options are based on a credit check of the putative patient, a credit score of the putative patient, or some combination thereof.

3. The method of claim 1, wherein the one or more financing options are based on a cost of the series of aligners.

4. The method of claim 1, wherein the one or more financing options are based on a treatment difficulty of the treatment plan.

5. The method of claim 1, further comprising instructing a digital device of the putative patient to: display an estimate of the treatment cost and a laboratory cost, schedule one or more appointments with the dental practitioner, display the one or more financing options, or some combination thereof.

6. The method of claim 1, further comprising providing the acceptance of the specific financing option to a user interface of a digital device of the putative patient.

7. The method of claim 1, further comprising instructing a digital device of the putative patient to display user-identifying information about the putative patient and one or more loan amounts.

8. The method of claim 1, further comprising instructing a digital device of the putative patient to display information about one or more merchants to assign to a loan.

9. The method of claim 1, further comprising alerting the dental appliance laboratory in response to the acceptance of the specific financing option.

10. The method of claim 1, further comprising alerting the dental practitioner in response to the acceptance of the specific financing option.

11. The method of claim 1, further comprising receiving a request to pre-approve the putative patient for a maximum financed amount.

12. The method of claim 1, further comprising:
receiving a request to pre-approve the putative patient for the treatment cost and a laboratory cost; and
providing a determination whether the putative patient has been pre-approved for the treatment cost and the laboratory cost.

13. The method of claim 1, further comprising:
receiving a request to pre-approve the putative patient for the treatment cost and a laboratory cost; and
providing a determination whether the putative patient has been pre-approved for the treatment cost and the laboratory cost;
wherein the one or more financing options are provided to the putative patient in response to the determination whether the putative patient has been pre-approved for the treatment cost and the laboratory cost.

14. The method of claim 1, further comprising receiving a request to pre-approve the putative patient for the treatment cost and a laboratory cost, wherein the request to pre-approve the putative patient comprises: a request for a credit score related to the putative patient, a request for a credit check related to the putative patient, or some combination thereof.

15. The method of claim 1, further comprising receiving a request to pre-approve the putative patient for the treatment cost and a laboratory cost before the putative patient has seen the dental practitioner.

16. The method of claim 1, further comprising receiving a request to pre-approve the putative patient for the treatment cost and a laboratory cost, wherein the request to pre-approve the putative patient is from the putative patient, the dental practitioner, or some combination thereof.

17. The method of claim 1, further comprising:
providing the putative patient with an electronic message containing a request to start a credit application;
receiving personal identifying information related to the putative patient in response to the electronic message; and
using the personal identifying information to pre-approve the putative patient person for the treatment cost and a laboratory cost.

18. The method of claim 1, further comprising:
obtaining patient identifying information related to the putative patient; and
pre-approving the putative patient for the treatment cost and a laboratory cost using the patient identifying information.

19. The method of claim 1, wherein the one or more financing options comprise one or more financing amounts less than a maximum financed amount that the putative patient has been pre-approved for.

20. The method of claim 1, further comprising instructing the dental appliance laboratory to manufacture the series of aligners in response to the acceptance of the specific financing option.

21. The method of claim 1, further comprising:
instructing the dental appliance laboratory to manufacture the series of aligners in response to the acceptance of the specific financing option; and
receiving a notification from the dental appliance laboratory representing when the series of dental appliances have been manufactured.

22. The method of claim 1, wherein providing the acceptance of the specific financing option by the putative patient comprises entering patient identifying information, a preapproval status, or a maximum financed amount for the treatment plan into the database.

23. The method of claim 1, wherein providing the acceptance of the specific financing option by the putative patient comprises updating the database to indicate funding of the actual financed amount of the treatment plan.

24. The method of claim 1, wherein the one or more financing options are determined by a remote financing server managed by a third-party that provides a loan to the putative patient.

25. A system including a financing server in communication with a putative patient, a dental appliance laboratory and a dental practitioner, the system comprising:
- one or more processors;
- memory coupled to the one or more processors, the memory storing computer-program instructions that, when executed by the one or more processors, cause the financing server to perform a computer-implemented method comprising:
  - updating a database of the financing server to indicate that the putative patient is pre-approved for a treatment loan;
  - establishing, by the financing server, different levels of access to the database for the dental appliance laboratory and the dental practitioner, wherein master access to the database is provided to the dental appliance laboratory, and client access to the database is provided to the dental practitioner, wherein the master access provides the dental appliance laboratory with an ability to monitor the database by receiving alerts from the financing server regarding different stages of the putative patient's financing;
  - receiving, from the dental practitioner, a treatment cost representing a cost of the dental practitioner to implement a treatment plan for treating the putative patient's dentition using a series of dental appliances;
  - providing, to the dental appliance laboratory, a first alert indicating that the treatment cost from the dental practitioner was received by the financing server;
  - receiving, from the dental practitioner or the putative patient, an acceptance of a specific financing option;
  - providing, to the dental appliance laboratory, a second alert indicating that funding for an actual financed amount for the putative patient has been received; and
- triggering payment to the dental practitioner and the dental appliance laboratory in response to receiving an indication from dental appliance laboratory that a treatment order has been fulfilled.

26. The system of claim 25, wherein instructing whether or not to implement the treatment plan comprises instructing the dental practitioner whether or not to approve the treatment plan.

27. The system of claim 25, wherein instructing as to whether or not to implement the treatment plan comprises instructing the dental appliance laboratory whether or not to initiate fabrication of the series of aligners.

28. The system of claim 25, further comprising obtaining a scan of the dentition of the putative patient by the dental practitioner.

29. The system of claim 25, further comprising fabricating the series of aligners by the dental appliance laboratory.

* * * * *